United States Patent [19]

Dotson et al.

[11] Patent Number: 5,254,801
[45] Date of Patent: Oct. 19, 1993

[54] HETEROLOGOUS DOMINANT CONDITIONAL LETHAL GENE WHICH IS A PHOSPHONATE MONOESTER HYDROLASE AND USE THEREOF IN PLANTS

[75] Inventors: Stanton B. Dotson, Fenton; Ganesh M. Kishore, Chesterfield, both of Mo.

[73] Assignee: Monsanto Company, St. Louis, Mo.

[21] Appl. No.: 621,670

[22] Filed: Dec. 3, 1990

[51] Int. Cl.$^5$ .......... A01H 4/00; C12N 5/14; C12N 15/82
[52] U.S. Cl. .............. 800/205; 435/240.4; 435/172.3; 435/320.1; 435/69.1; 935/64; 935/67; 800/DIG. 15
[58] Field of Search ......... 800/205, DIG. 15; 435/320.1, 172.3, 240.4, 69.1; 536/27; 935/64, 67

[56] References Cited

PUBLICATIONS

Fitzgibbon (Dec. 1988) University Microfilms International 1989, Abstract.
Fitzgibbon et al. (Nov. 1990) Applied and Environmental Microbiology 56(11): 3382–3388.
Moore, et al. (Aug. 1983) Applied and Environmental Microbiology 46: 316–320.
Lee, et al. (1988) Science 239: 1288–1291.
Walden, et al. (1990) Eur. J. Biochem 192: 563–564.
Mariani, et al. (Oct. 1990) Nature 347: 737–741.
Shinabarger, et al. (Nov. 1984) Applied and Environmenal Microbiology 48(5): 1049–1050.

*Primary Examiner*—Che S. Chereskin
*Attorney, Agent, or Firm*—Dennis R. Hoerner, Jr.; Howard C. Stanley

[57] ABSTRACT

A class of heterologous dominant conditional lethal genes is disclosed. The gene is useful in genetically modifying plant cells and plants to selectively induce cellular lethality for purposes such as inducing male sterility for hybrid seed production, cell ablation and counter-negative selection.

20 Claims, 10 Drawing Sheets

```
   1  ATGACCAGAA  AAAATGTCCT  GCTTATCGTC  GTTGATCAAT    40
  41  GGCGAGCAGA  TTTTATCCCT  CACCTGATGC  GGGCGGAGGG    80
  81  GCGCGAACCT  TTCCTTAAAA  CTCCCAATCT  TGATCGTCTT   120
 121  TGCCGGGAAG  GCTTGACCTT  CCGCAATCAT  GTCACGACGT   160
 161  GCGTGCCGTG  TGGTCCGGCA  AGGGCAAGCC  TGCTGACGGG   200
 201  CCTCTACCTG  ATGAACCACC  GGGCGGTGCA  GAACACTGTT   240
 241  CCGCTTGACC  AGCGCCATCT  AAACCTTGGC  AAGGCCCTGC   280
 281  GCGCCATTGG  CTACGATCCC  GCGCTCATTG  GTTACACCAC   320
 321  CACGACACCT  GATCCGCGCA  CAACCTCTGC  AAGGGATCCG   360
 361  CGTTTCACGG  TCCTGGGCGA  CATCATGGAC  GGCTTTCGTT   400
 401  CGGTCGGCGC  ATTCGAGCCC  AATATGGAGG  GGTATTTTGG   440
 441  CTGGGTGGCG  CAGAACGGCT  TCGAACTGCC  AGAGAACCGC   480
 481  GAAGATATCT  GGCTGCCGGA  AGGTGAACAT  TCCGTTCCCG   520
 521  GTGCTACCGA  CAAACCGTCG  CGCATTCCGA  AGGAATTTTC   560
 561  GGATTCGACA  TTCTTCACGG  AGCGCGCCCT  GACATATCTG   600
 601  AAGGGCAGGG  ACGGCAAGCC  TTTCTTCCTG  CATCTTGGCT   640
 641  ATTATCGCCC  GCATCCGCCT  TTCGTAGCCT  CCGCGCCCTA   680
 681  CCATGCGATG  TACAAAGCCG  AAGATATGCC  TGCGCCTATA   720
 721  CGTGCGGAGA  ATCCGGATGC  CGAAGCGGCA  CAGCATCCGC   760
 761  TCATGAAGCA  CTATATCGAC  CACATCAGAC  GCGGCTCGTT   800
 801  CTTCCATGGC  GCGGAAGGCT  CGGGAGCAAC  GCTTGATGAA   840
 841  GGCGAAATTC  GCCAGATGCG  CGCTACATAT  TGCGGACTGA   880
 881  TCACCGAGAT  CGACGATTGT  CTGGGGAGGG  TCTTTGCCTA   920
 921  TCTCGATGAA  ACCGGTCAGT  GGGACGACAC  GCTGATTATC   960
 961  TTCACGAGCG  ATCATGGCGA  ACAACTGGGC  GATCATCACC  1000
1001  TGCTCGGCAA  GATCGGTTAC  AATGCCGAAA  GCTTCCGTAT  1040
1041  TCCCTTGGTC  ATAAAGGATG  CGGGACAGAA  CCGGCACGCC  1080
1081  GGCCAGATCG  AAGAAGGCTT  CTCCGAAAGC  ATCGACGTCA  1120
1121  TGCCGACCAT  CCTCGAATGG  CTGGGCGGGG  AAACGCCTCG  1160
1161  CGCCTGCGAC  GGCCGTTCGC  TGTTGCCGTT  TCTGGCTGAG  1200
1201  GGAAAGCCCT  CCGACTGGCG  CACGGAACTA  CATTACGAGT  1240
1241  TCGATTTTCG  CGATGTCTTC  TACGATCAGC  CGCAGAACTC  1280
1281  GGTCCAGCTT  TCCCAGGATG  ATTGCAGCCT  CTGTGTGATC  1320
1321  GAGGACGAAA  ACTACAAGTA  CGTGCATTTT  GCCGCCCTGC  1360
1361  CGCCGCTGTT  CTTCGATCTG  AAGGCAGACC  CGCATGAATT  1400
1401  CAGCAATCTG  GCTGGCGATC  CTGCTTATGC  GGCCCTCGTT  1440
1441  CGTGACTATG  CCCAGAAGGC  ATTGTCGTGG  CGACTGTCTC  1480
1481  ATGCCGACCG  GACACTCACC  CATTACAGAT  CCAGCCCGCA  1520
1521  AGGGCTGACA  ACGCGCAACC  ATTGA  1545
```

Figure 2.

```
   1  ATCGATNNNN  NNNNNNNNNN  NNNNNNNNNN  NNNNNNNNNN    40
  41  NNNNNNNNNN  NNNNNNNNNN  NNNNNNNNNN  NNNNNNNNNN    80
  81  NNNNNNNNNN  NNNNNNNNNN  NNNNNNNNNN  NNNNNNNNNN   120
 121  NNNNNNNNNN  NNNNNNNNNN  NNNNNNNNNN  NNNNNNNNNN   160
 161  NNNNNNNNNN  NNNNNNNNNN  NNNNNNNNNN  NNNNNNNNNN   200
 201  NNNNNNNNNN  NNNNNNNNNN  NNNNNNNNNN  NNNNNNNNNN   240
 241  NNNNNNNNNN  NNNNNNNNNN  NNNNNNNNNN  NNNNNNNNNN   280
 281  NNNNNNNNNN  NNNNNNNNNN  NNNNNNNNNN  NNNNNNNNNN   320
 321  NNNNNNNNNN  NNNNNNNNNN  NNNNNNNNNN  NNNNNNNNNN   360
 361  NNNNNNNNNN  NNNNNNNNNN  NNNNNNNNNN  NNNNNNNNNN   400
 401  NNNNNNNNNN  NNNNNNNNNN  NNNNNNNNNN  NNNNNNNNNN   440
 441  NNNNNNNNNN  NNNNNNNNNN  NNNNNNNNNN  NNNNNNNNNN   480
 481  NNNNNNNNNN  NNNNNNNNNN  NNNNNNNNNN  NNNNNNNNNN   520
 521  NNNNNNNNNN  NNNNNNNNNN  NNNNNNNNNN  NNNNNNNNNN   560
 561  NNNNNNNNNN  NNNNNNNNNN  NNNNNNNNNN  NNNNNNNNNN   600
 601  NGACCTCATT  CGTTCTGATA  TATAACATGT  TAATTAACGA   640
 641  AATTGTGTGT  AACTATTTCA  TCTAGAAATT  TAAGTTACTG   680
 681  GATAGAGTAT  GAAAACAGTA  AGAAGTTGTT  AAAGTTAAAA   720
 721  ATGATAAGAT  CTTATTATAA  ATTAATTATA  TTGAATCTTA   760
 761  TAATATAAGT  TATGCAATTT  GAGTTGTTTG  ATGTGTGTTA   800
 801  AGACTTAGGT  TGATCATGTA  GTCGAGAAGG  TGTTAATTAA   840
 841  AGTATGTCTA  TGGAAAGATG  TAGTTGGCTT  CTTTTTCTTT   880
 881  TTTCCCTCTC  TATATAGTAC  ATGATGACTA  TGTTACACAC   920
 921  AATATGTATG  AGCTAGTGAT  ATTTCTACCT  TCAAATTCT    960
 961  TCATTATTGT  ACCAATTTTT  GGACACCTAT  ATAACTTGAG  1000
1001  CTTGCAAATC  CAAATATTCT  CACACTCAAA  ACATCATACA  1040
1041  ATATTAATTA  CTCTTTTCTT  CTACCTAGGC  AAAATGGCAA  1080
1081  CCACGATTCT  TGTTGTTATT  CTTATTATCA  CTAGTGTTCT  1120
1121  TACTTACCCT  ATAAATGCGA  GGACGCTAAT  GGCAATGAAG  1160
1161  GAAAAACCAA  AAGCATCAGC  TGATGAACAG  AATGAATATT  1200
1201  TCCAGCACCC  TTTATCGCCT  TTTTTGGTG   GTTTTGGTGG  1240
1241  TGTTAGAGGT  GCAATTAGGC  CTCCATTTGG  TTTAGGAGCC  1280
1281  GGCTTTGGTG  GATTTGGTGG  TAGTATTGGA  GGTGCTTTTG  1320
1321  GAAGTGGTTT  TGGTCCTTTC  GCCGGAAATG  GTGGAACAAG  1360
1361  TAGTGCTAGA  AGTGGAAGTG  GAAGTGGAAG  TGGATTTGGT  1400
1401  TCTGGTATTA  ATGAAGGGTT  TGGAAATAAT  GGTGGCAATA  1440
1441  ATCCTAATGA  TAAAATTGAA  GGTGAACTTG  ATACAGGTGA  1480
1481  CCTAGGTGAG  GGAGGTGATG  CAACAATTAA  AAATGATATG  1520
1521  CACCACCATT  GAACTTAAAC  TCACTAATTA  TTAATAAAAG  1560
1561  ATTGCTAAAT  CATAGCATCT  AGTAGTATNN  NNNNNNNNNN  1600
1601  NNGAATTC  1608
```

Figure 5.

SEQUENCE LISTING ( 1 ) GENERAL INFORMATION:

( i i i ) NUMBER OF SEQUENCES: 22

( 2 ) INFORMATION FOR SEQ ID NO:1:

( i ) SEQUENCE CHARACTERISTICS:
        ( A ) LENGTH: 1545 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

```
ATGACCAGAA AAAATGTCCT GCTTATCGTC GTTGATCAAT GGCGAGCAGA TTTTATCCCT      60
CACCTGATGC GGGCGGAGGG GCGCGAACCT TTCCTTAAAA CTCCCAATCT TGATCGTCTT     120
TGCCGGGAAG GCTTGACCTT CCGCAATCAT GTCACGACGT GCGTGCCGTG TGGTCCGGCA     180
```

| | | | | | | |
|---|---|---|---|---|---|---|
| AGGGCAAGCC | TGCTGACGGG | CCTCTACCTG | ATGAACCACC | GGGCGGTGCA | GAACACTGTT | 240 |
| CCGCTTGACC | AGCGCCATCT | AAACCTTGGC | AAGGCCCTGC | GCGCCATTGG | CTACGATCCC | 300 |
| GCGCTCATTG | GTTACACCAC | CACGACACCT | GATCCGCGCA | CAACCTCTGC | AAGGGATCCG | 360 |
| CGTTTCACGG | TCCTGGGCGA | CATCATGGAC | GGCTTTCGTT | CGGTCGGCGC | ATTCGAGCCC | 420 |
| AATATGGAGG | GGTATTTTGG | CTGGGTGGCG | CAGAACGGCT | TCGAACTGCC | AGAGAACCGC | 480 |
| GAAGATATCT | GGCTGCCGGA | AGGTGAACAT | TCCGTTCCCG | GTGCTACCGA | CAAACCGTCG | 540 |
| CGCATTCCGA | AGGAATTTTC | GGATTCGACA | TTCTTCACGG | AGCGCGCCCT | GACATATCTG | 600 |
| AAGGGCAGGG | ACGGCAAGCC | TTTCTTCCTG | CATCTTGGCT | ATTATCGCCC | GCATCCGCCT | 660 |
| TTCGTAGCCT | CCGCGCCCTA | CCATGCGATG | TACAAAGCCG | AAGATATGCC | TGCGCCTATA | 720 |
| CGTGCGGAGA | ATCCGGATGC | CGAAGCGGCA | CAGCATCCGC | TCATGAAGCA | CTATATCGAC | 780 |
| CACATCAGAC | GCGGCTCGTT | CTTCCATGGC | GCGGAAGGCT | CGGGAGCAAC | GCTTGATGAA | 840 |
| GGCGAAATTC | GCCAGATGCG | CGCTACATAT | TGCGGACTGA | TCACCGAGAT | CGACGATTGT | 900 |
| CTGGGGAGGG | TCTTTGCCTA | TCTCGATGAA | ACCGGTCAGT | GGGACGACAC | GCTGATTATC | 960 |
| TTCACGAGCG | ATCATGGCGA | ACAACTGGGC | GATCATCACC | TGCTCGGCAA | GATCGGTTAC | 1020 |
| AATGCCGAAA | GCTTCCGTAT | TCCCTTGGTC | ATAAAGGATG | CGGGACAGAA | CCGGCACGCC | 1080 |
| GGCCAGATCG | AAGAAGGCTT | CTCCGAAAGC | ATCGACGTCA | TGCCGACCAT | CCTCGAATGG | 1140 |
| CTGGGCGGGG | AAACGCCTCG | CGCCTGCGAC | GGCCGTTCGC | TGTTGCCGTT | TCTGGCTGAG | 1200 |
| GGAAAGCCCT | CCGACTGGCG | CACGGAACTA | CATTACGAGT | TCGATTTTCG | CGATGTCTTC | 1260 |
| TACGATCAGC | CGCAGAACTC | GGTCCAGCTT | TCCCAGGATG | ATTGCAGCCT | CTGTGTGATC | 1320 |
| GAGGACGAAA | ACTACAAGTA | CGTGCATTTT | GCCGCCCTGC | CGCCGCTGTT | CTTCGATCTG | 1380 |
| AAGGCAGACC | CGCATGAATT | CAGCAATCTG | GCTGGCGATC | CTGCTTATGC | GGCCCTCGTT | 1440 |
| CGTGACTATG | CCCAGAAGGC | ATTGTCGTGG | CGACTGTCTC | ATGCCGACCG | GACACTCACC | 1500 |
| CATTACAGAT | CCAGCCCGCA | AGGGCTGACA | ACGCGCAACC | ATTGA | | 1545 |

( 2 ) INFORMATION FOR SEQ ID NO:2:

( i ) SEQUENCE CHARACTERISTICS:
        ( A ) LENGTH: 1608 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:2:

| | | | | | | |
|---|---|---|---|---|---|---|
| ATCGATNNNN | NNNNNNNNNN | NNNNNNNNNN | NNNNNNNNNN | NNNNNNNNNN | NNNNNNNNNN | 60 |
| NNNNNNNNNN | NNNNNNNNNN | NNNNNNNNNN | NNNNNNNNNN | NNNNNNNNNN | NNNNNNNNNN | 120 |
| NNNNNNNNNN | NNNNNNNNNN | NNNNNNNNNN | NNNNNNNNNN | NNNNNNNNNN | NNNNNNNNNN | 180 |
| NNNNNNNNNN | NNNNNNNNNN | NNNNNNNNNN | NNNNNNNNNN | NNNNNNNNNN | NNNNNNNNNN | 240 |
| NNNNNNNNNN | NNNNNNNNNN | NNNNNNNNNN | NNNNNNNNNN | NNNNNNNNNN | NNNNNNNNNN | 300 |
| NNNNNNNNNN | NNNNNNNNNN | NNNNNNNNNN | NNNNNNNNNN | NNNNNNNNNN | NNNNNNNNNN | 360 |
| NNNNNNNNNN | NNNNNNNNNN | NNNNNNNNNN | NNNNNNNNNN | NNNNNNNNNN | NNNNNNNNNN | 420 |
| NNNNNNNNNN | NNNNNNNNNN | NNNNNNNNNN | NNNNNNNNNN | NNNNNNNNNN | NNNNNNNNNN | 480 |
| NNNNNNNNNN | NNNNNNNNNN | NNNNNNNNNN | NNNNNNNNNN | NNNNNNNNNN | NNNNNNNNNN | 540 |
| NNNNNNNNNN | NNNNNNNNNN | NNNNNNNNNN | NNNNNNNNNN | NNNNNNNNNN | NNNNNNNNNN | 600 |
| NGACCTCATT | CGTTCTGATA | TATAACATGT | TAATTAACGA | AATTGTGTGT | AACTATTTCA | 660 |

-continued

| | | | | | | |
|---|---|---|---|---|---|---|
| TCTAGAAATT | TAAGTTACTG | GATAGAGTAT | GAAAACAGTA | AGAAGTTGTT | AAAGTTAAAA | 720 |
| ATGATAAGAT | CTTATTATAA | ATTAATTATA | TTGAATCTTA | TAATATAAGT | TATGCAATTT | 780 |
| GAGTTGTTTG | ATGTGTGTTA | AGACTTAGGT | TGATCATGTA | GTCGAGAAGG | TGTTAATTAA | 840 |
| AGTATGTCTA | TGGAAAGATG | TAGTTGGCTT | CTTTTTCTTT | TTTCCCTCTC | TATATAGTAC | 900 |
| ATGATGACTA | TGTTACACAC | AATATGTATG | AGCTAGTGAT | ATTTCTACCT | TTCAAATTCT | 960 |
| TCATTATTGT | ACCAATTTTT | GGACACCTAT | ATAACTTGAG | CTTGCAAATC | CAAATATTCT | 1020 |
| CACACTCAAA | ACATCATACA | ATATTAATTA | CTCTTTTCTT | CTACCTAGGC | AAAATGGCAA | 1080 |
| CCACGATTCT | TGTTGTTATT | CTTATTATCA | CTAGTGTTCT | TACTTACCCT | ATAAATGCGA | 1140 |
| GGACGCTAAT | GGCAATGAAG | GAAAAACCAA | AAGCATCAGC | TGATGAACAG | AATGAATATT | 1200 |
| TCCAGCACCC | TTTATCGCCT | TTTTTGGTG | GTTTTGGTGG | TGTTAGAGGT | GCAATTAGGC | 1260 |
| CTCCATTTGG | TTTAGGAGCC | GGCTTTGGTG | GATTTGGTGG | TAGTATTGGA | GGTGCTTTTG | 1320 |
| GAAGTGGTTT | TGGTCCTTTC | GCCGGAAATG | GTGGAACAAG | TAGTGCTAGA | AGTGGAAGTG | 1380 |
| GAAGTGGAAG | TGGATTTGGT | TCTGGTATTA | ATGAAGGGTT | TGGAAATAAT | GGTGGCAATA | 1440 |
| ATCCTAATGA | TAAAATTGAA | GGTGAACTTG | ATACAGGTGA | CCTAGGTGAG | GGAGGTGATG | 1500 |
| CAACAATTAA | AAATGATATG | CACCACCATT | GAACTTAAAC | TCACTAATTA | TTAATAAAAG | 1560 |
| ATTGCTAAAT | CATAGCATCT | AGTAGTATNN | NNNNNNNNN | NNGAATTC | | 1608 |

( 2 ) INFORMATION FOR SEQ ID NO:3:

( i ) SEQUENCE CHARACTERISTICS:
        ( A ) LENGTH: 35 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 13
        ( D ) OTHER INFORMATION: /label=Ambiguous AA
            / note="Amino acid listed is most probable
            estimate."

( x i ) SEQUENCE DESCRIPTION: SEQ ID NO:3:

Xaa Arg Lys Asn Val Leu Leu Ile Val Val Asp Gln Cys Arg Ala Asp
1               5                   10                  15

Phe Ile Pro His Leu Met Arg Ala Glu Gly Arg Glu Pro Phe Leu Xaa
            20                  25                  30

Xaa Pro Asn
        35

( 2 ) INFORMATION FOR SEQ ID NO:4:

( i ) SEQUENCE CHARACTERISTICS:
        ( A ) LENGTH: 10 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 10
        ( D ) OTHER INFORMATION: /label=Ambiguous AA
            / note="Amino acid listed is most probable
            estimate."

( x i ) SEQUENCE DESCRIPTION: SEQ ID NO:4:

Xaa Xaa Gly Ala Phe Glu Ala Asn Xaa Gln (2) INFORMATION FOR SEQ ID NO:5:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:5:

```
Glu Asp Ile Trp Leu Pro Glu Gly Glu His Ser Val Pro Gly Ala Thr
1               5                   10                  15
Asp Lys Pro Ser Arg
            20
```

(2) INFORMATION FOR SEQ ID NO:6:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Ala Tyr Leu Asp Glu Thr Gly Gln
1               5
```

(2) INFORMATION FOR SEQ ID NO:7:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:7:

```
Ala Ala Gly Gln Asp Glu Ala Ile Asn Xaa Glu
1               5                   10
```

(2) INFORMATION FOR SEQ ID NO:8:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 6
        (D) OTHER INFORMATION: /label=Ambiguous AA
            / note="Unambiguous assignment not possible - most probable estimate is a cysteine/glutamic acid mixture."

(xi) SEQUENCE DESCRIPTION: SEQ ID NO:8:

```
Xaa Ala Gly Gln Asp Xaa Ala Ile Asn Xaa Glu
1               5                   10
```

(2) INFORMATION FOR SEQ ID NO:9:

(i) SEQUENCE CHARACTERISTICS:
        (A) LENGTH: 42 base pairs
        (B) TYPE: nucleic acid (C) STRANDEDNESS: single
(D) TOPOLOGY: linear (ii) MOLECULE TYPE: DNA (synthetic)

(xi) SEQUENCE DESCRIPTION: SEQ ID NO:9:

ATCGTRGATC AGTGCCGCGC AGATTTCATC CCGCATCTAA TG 42

(2) INFORMATION FOR SEQ ID NO:10:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (ii) MOLECULE TYPE: DNA (synthetic)

(xi) SEQUENCE DESCRIPTION: SEQ ID NO:10:

GARGAYATYT GGCTNCC 18

(2) INFORMATION FOR SEQ ID NO:11:

(i) SEQUENCE CHARACTERISTICS:
 (A) LENGTH: 17 base pairs
 (B) TYPE: nucleic acid
 (C) STRANDEDNESS: single
 (D) TOPOLOGY: linear (ii) MOLECULE TYPE: DNA (synthetic)

(xi) SEQUENCE DESCRIPTION: SEQ ID NO:11:

GARGAYATYT GGTTRCC 17

(2) INFORMATION FOR SEQ ID NO:12:

(i) SEQUENCE CHARACTERISTICS:
 (A) LENGTH: 26 base pairs
 (B) TYPE: nucleic acid
 (C) STRANDEDNESS: single
 (D) TOPOLOGY: linear (ii) MOLECULE TYPE: DNA (synthetic)

(xi) SEQUENCE DESCRIPTION: SEQ ID NO:12:

GARGAYATYT GGCTGCCSGA RGGYCA 26

(2) INFORMATION FOR SEQ ID NO:13:

(i) SEQUENCE CHARACTERISTICS:
 (A) LENGTH: 14 base pairs
 (B) TYPE: nucleic acid
 (C) STRANDEDNESS: single
 (D) TOPOLOGY: linear (ii) MOLECULE TYPE: DNA (synthetic)

(xi) SEQUENCE DESCRIPTION: SEQ ID NO:13:

TGRCCSGTYT CRTC 14

(2) INFORMATION FOR SEQ ID NO:14:

(i) SEQUENCE CHARACTERISTICS:
 (A) LENGTH: 12 amino acids
 (B) TYPE: amino acid
 (C) STRANDEDNESS: single
 (D) TOPOLOGY: linear (ii) MOLECULE TYPE: peptide (xi) SEQUENCE DESCRIPTION: SEQ ID NO:14:

```
        His  Ser  Val  Pro  Gly  Ala  Thr  Asp  Lys  Xaa  Xaa  Arg
        1              5                        10
```

( 2 ) INFORMATION FOR SEQ ID NO:15:

( i ) SEQUENCE CHARACTERISTICS:
        ( A ) LENGTH: 21 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:15:

```
        Glu  Asp  Ile  Trp  Leu  Pro  Glu  Gly  Glu  His  Ser  Val  Pro  Gly  Ala  Thr
        1              5                        10                       15

Asp  Lys  Pro  Ser  Arg
                        20
```

( 2 ) INFORMATION FOR SEQ ID NO:16:

( i ) SEQUENCE CHARACTERISTICS:
        ( A ) LENGTH: 48 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:16:

GTAAGCCTCG GAAATAAAGA TCTCACCATG GCCAGAAAAA ATGTCCTG          48

( 2 ) INFORMATION FOR SEQ ID NO:17:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:17:

TTGCTCCTGA GCTCAATGGT TGC          23

( 2 ) INFORMATION FOR SEQ ID NO:18:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:18:

GAAACGCGGA TCTCTTGCAG AGGT          24

( 2 ) INFORMATION FOR SEQ ID NO:19:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: DNA (synthetic)

( x i ) SEQUENCE DESCRIPTION: SEQ ID NO:19:

ATACGGAAGC TCTCGGCATT GTA          23

(2) INFORMATION FOR SEQ ID NO:20:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:20:

GAGCCTTCCG CACCATGAAA GAACGAGCC        29

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:21:

CAGATTGCTG AACTCATGCG GGTC        24

(2) INFORMATION FOR SEQ ID NO:22:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: DNA (synthetic)

(xi) SEQUENCE DESCRIPTION: SEQ ID NO:22:

AATCGTGGTT GCCATGGTGC CTAGG        25

HETEROLOGOUS DOMINANT CONDITIONAL LETHAL GENE WHICH IS A PHOSPHONATE MONOESTER HYDROLASE AND USE THEREOF IN PLANTS

This invention relates in general to plant molecular biology and, more particularly, to a class of phosphonate monoester hydrolases which are useful as heterologous dominant conditional lethal genes.

BACKGROUND OF THE INVENTION

Recent advances in genetic engineering have provided the requisite tools to transform plants to contain foreign genes. It is now possible to genetically improve plants to have unique characteristics of agronomic importance. Certainly, one such advantageous trait is controlled plant cell lethality. Expression of a lethal gene in a cell can be used to specifically kill or prevent development of that targeted cell type from within an organism or from within a population of cells. A lethal gene has potential applications for hybrid seed production, cell ablation, and negative (counter) selection.

To be generally useful, lethal genes must be expressible behind a variety of promoters, be effective in a variety of cell types and be cell autonomous. Both dominant and conditional (inducible) lethal genes have been described in the literature. Dominant lethal genes include the expression of a protein which is directly toxic such as ricin which inhibits ribosomes (Landel et al., 1988), diphtheria toxin A (Dip-A gene) which ADP-ribosylates elongation factor 2 (Palmiter et al., 1987) and RNAses and DNAses which degrade critical genetic molecules (Mariani et al., 1990). Dominant lethal genes may also include antisense and ribozyme genes which target RNA molecules for critical cellular processes. The advantage of such dominant lethal genes is good efficacy and strict cell autonomous expression. The use of dominant lethal genes is severely restricted when expression of the lethal gene is critical for the survival or reproduction of the organism preventing the development of true-breeding progeny.

A conditional lethal phenotype involves the expression of a gene product which is not lethal to a cell in a normal environment but becomes lethal in a controlled environment. A conditionally lethal gene might encode a protein which converts an inactive or less active protoxin into a cytotoxic product or encode a biological molecule which prevents expression of a protein normally present to protect the cell from a toxin. The following discussion on conditional lethal genes will be in the context of a gene which converts a protoxin substrate into a cytotoxic product. The conditional lethal gene has several advantages over a dominant lethal gene. First, true breeding progeny can be obtained which express the conditional lethal gene without ill effects on the plants in the absence of the protoxin. Second, the timing and specificity for cell lethality can be controlled by both the expression of the gene and the application of the protoxin. Third, the efficacy of the conditional lethal gene can also be controlled by modifications to the protoxin if the activating enzyme encoded by this gene has a broad substrate specificity. Examples of conditional lethal genes used in plant studies include nitrate reductase which converts chlorate to toxic chlorite (Mueller and Grafe, 1978) and alcohol dehydrogenase which activates allyl alcohol (Schwartz and Osterman, 1976). However, these enzymes are normally expressed by wild-type cells limiting their use to cells which carry null mutations in the wild-type genes. Heterologous dominant conditional lethal genes have the greatest potential for controlled cell lethality. The genes are by definition, non-lethal in the absence of the controlled application of a heterologous protoxin and utilize protoxins which are not substrates for normal cellular enzymes. In plants, the only example of a heterologous conditional lethal gene is the iaaH gene encoding indoleacetamide hydrolase which can convert non-toxic levels of naphthalene acetamide into toxic levels of the auxin, naphthalene acetic acid (Klee et al., 1987). Since naphthalene acetamide is itself toxic at high levels, the conditional lethal phenotype is difficult to control. Viral thymidine kinase is an example of a heterologous dominant conditional lethal gene in mammalian cells. Unlike the cellular thymidine kinase, the viral thymidine kinase protein is able to activate pyrimidine analogs such as acycolvir and gancyclovia into toxic products (Elion, 1978 and Mansour et al., 1988). As described below, a novel conditional lethal gene is needed in plant biology which, has no affect on cellular metabolism in the absence of protoxin, utilizes a protoxin which is several orders of magnitude less toxic than the activated toxin, has a unique substrate specificity distinct from plant cellular enzymes and which utilizes a protoxin inexpensive to synthesize on a large scale.

HYBRID SEED PRODUCTION

Plant breeders can design a cross between two parents such that the progeny outperform both of the parents. This increased performance is from heterosis or hybrid vigour. The increased yield associated with hybrid vigour makes hybrid seed profitable for farmer to purchase seed each year rather than saving seed from the previous year and profitable for a plant breeding company to sell hybrid seed. Heterosis has been identified in all major crop species, however most crops are not currently amenable to commercial hybrid seed production which requires three additional criteria. There must be a method to remove fertile pollen from the female parent. Pollen from the male parent must be effectively transported from the male parent to the male-sterile female line. And thirdly, hybrid seed must be produced reliably and economically (Fehr, 1987). Some plants, such as corn, can be relatively easily hybridized without resort to genetic techniques because the organ containing the male gametes are exposed and can be mechanically removed. These systems leave the female gametes, when ready for fertilization, accessible to any foreign corn pollen that is deposited thereon. However, a simple, reliable and economical method to achieve male sterility in the female parent while leaving the female gametes accessible for hybridization is the major limitation to hybrid seed production in most crop species, particularly in canola, oil seed rape, cotton and many cereal grains. Even for corn, mechanical detasseling is labor intensive and expensive providing an opportunity for cost of production improvements.

Several naturally occurring systems for male sterility are being studied extensively in corn, petunia, cotton, canola and other plants. In many instances, male sterility results from the developmental arrest of the pollen and/or the anther tissue which nourish the developing pollen grains and release the mature pollen with the correct timing. In the cytoplasmic T-type male sterility in maize, the mitochondria of the tapetal cell layer in the another degenerate prematurely (Lee and Warmke, 1979). Since the tapetal cell layer is critically involved in nourishing the developing pollen grains, the immature pollen cells fail to develop resulting in male sterility. The current hypothesis for the disintegration of the tapetal cell layer is the expression of a variant mitochondrial gene which is specifically cytotoxic to the tapetal cells. From this example and the many other examples of natural male sterility systems (for a review see Lasar and Larsten, 1972), one expects that transformation of a dominant lethal gene engineered for anther or pollen specific expression will result in male sterility. In fact, the expression of a dominant lethal gene in the developing another or pollen has recently been described (Mariani et al., 1990; Fabijanski, 1990). However, these techniques, using cytoplasmic male sterility and expression of a dominant lethal gene in developing anthers or pollen, are highly time consuming for development of elite parent lines to the point where commercial quantities of hybrid seed can be produced.

A gametocide is compound that when applied to a plant, is capable of killing or effectively terminating the development of a plant's male gametes while leaving the plant's female gametes, or at least a significant proportion of them, capable of undergoing cross fertilization with subsequent high yield of fertile, viable hybrid seed. The utility of gametocides lies in precisely this area of plant hybridization. By causing pollination of one variety of a plant species by a different variety of the same species, a hybrid plant may be obtained. By careful selection of the parents, hybrids can be obtained with hybrid vigour and specific combinations of desirable traits such as plant size, grain yield, disease resistance, herbicide tolerance, insect resistance, processing quality traits, and so on.

Many compounds are capable of killing the male gametes of a plant, indeed almost any systemic herbicide is effective in this role. However most also kill the female gametes and the reset of the plant and are therefore ineffective gametocides. Additionally, while some compounds can be applied at rates such that substantially only the gametes are affected, most are found to be fairly non-discriminating regarding the sex of the gametes destroyed.

A requirement of a useful gametocide, therefore, is that the application level at which male gametes are effectively destroyed should be significantly lower than the level which will also destroy the female gametes or vegetative plant tissues. Thus a gametocide should be capable of being spray applied in the field without extraordinary precautions against accidental overdoses and effective on a wide variety of genotypes.

Other desirable characteristics may be dictated by the plant to be treated. As an example, wheat is by nature self-pollinating as the male and female gametes are found inside the same flower which remains closed until the male gametes release their pollen onto the female gametes to fertilize them. Thus, when the flower opens fertilization is normally essentially complete. For a gametocide to be useful on wheat it must, besides killing the male gametes, not interfere with the opening of the flower when the female gametes are ready to be fertilized such that fertilization by pollen from other wheat plants can occur.

Unfortunately, commercially useful gametocides have been difficult to identify as evidenced by the lack of gametocidal use in commercial hybrid seed production to date. Development of gametocides has been difficult since many of the metabolic activities which occur in the anthers and male gametes also occur in the female gametes and vegetative tissues. In one respect, the present invention is based on the approach of using genetic engineering to express in the anthers or pollen a enzymatic activity which has substrate specificity not normally found in plants (a heterologous enzyme activity) which can be targeted to develop a more useful gametocidal compound. The method of the present invention specifically provides a gene encoding a phosphonate monoester hydrolase with a broad substrate specificity not normally found in plant cells and an exemplary promoter sequence which are useful for expressing a phosphonate monoester hydrolase gene specifically in developing anthers or pollen. The practice of the method of the present invention utilizes protoxin compounds which are relatively non-toxic but can be activated by the phosphonate monoester hydrolase enzyme activity to form cytotoxic compounds. Since in one aspect of the present invention dealing with hybrid seed production the heterologous enzyme activity is only expressed in the anthers or pollen, the protoxin will result in gametocidal activity without significant affect on the female gametes or vegetative tissues. This aspect of the present invention will be hereinafter referred to as conditional male sterility.

Conditional male sterility is distinct from the genetically engineered expression of dominant lethal genes and cytoplasmic male sterility mechanisms which have already been described in the literature. In these systems, a gene is expressed which is directly lethal or results in lethality of a normal, wild-type anther or pollen cell. Therefore, each generation during female parent line development will yield 50%-100% of the time sterile progeny. This increases the time for elite parental line development. Also, these male sterility systems require a second system to restore full male fertility in the hybrid seed which will be grown by the farmer. In the novel conditional male sterility method described herein, expression of the phosphonate monoester hydrolase normally does not result in lethality of a anther or pollen cell which facilitates the development of elite parental lines and eliminates the requirement for a fertility restoration system in the hybrid seed. Male sterility is induced by the application of the protoxin only when desirable such as in a commercial hybrid seed production field.

CELL ABLATION

An important area of plant scientific research is cell lineage formation and organogenesis. The development of a cell lineage can be followed by transformation of a visible marker protein such as $\beta$-glucuronidase (Jefferson et al., 1987) or by inducing null mutations in pigment proteins (for a review see Poethig, 1987). However, using a visible marker does not answer questions concerning the critical events in developmental timing or the influence of neighboring cells on development or the dependence of a organism on a particular differentiated tissue. Such questions can be answered with the genetic approach of cell ablation. Specifically, a lethal gene or conditional lethal gene is expressed behind a promoter element. The promoter element is identified and isolated based on its tissue-specific and/or developmental timing-specific expression of a fused coding sequence. Cell lineage development can then be arrested or destroyed and the effects on the organ or organism can be studied.

Cell ablation also has practical applications. Male sterility is a specific example of cell ablation as described above. Many crops are grown specifically for the vegetative parts such as potato, carrots, alfalfa and so on. Reproductive organs which require a tremendous amount of plant resources can be specifically targeted by cell ablation and may allow those resources to be redirected into the economically important tissues. In theory, any organ which is not desirable can be developmentally arrested or destroyed using cell ablation.

COUNTER (NEGATIVE) SELECTION

In many genetic and cell culture studies, cells or organisms of an incorrect genotype need to be removed from the population. Cells or organisms with an undesirable genotype can be tagged with a conditional lethal gene such as the phosphonate monoester hydrolase gene of the present invention. In the presence of the protoxin those cells or organisms expressing the negative selectable marker gene will be arrested or killed while wild-type cells or organisms continue to divide or develop. For example, a negative selectable marker can be used to enrich for a transformed cell type which has undergone homologous recombination (Mansour et al., 1988).

A conditional lethal gene such as the phosphonate ester hydrolase gene of the present invention can be used to select for mutations in transcription factors. In this example, the conditional lethal gene is fused to a promoter of interest and multiple copies of the expression cassette (promoter fused to the coding sequence with a polyA signal) are transformed into a cell line or organism. The cell line or organism is then mutagenized and if possible, each mutagenized line is assayed to insure the promoter-lethal gene fusion is still active after mutagenesis. Resulting mutant populations are then subjected to negative selection by the application of the protoxin. Those surviving negative selection will be screened to identify lines which carry a mutation in a transcription activation factor such that the promoter no longer expresses the conditional lethal gene. Once identified, these transcription factors can be studied and manipulated by standard approaches.

SUMMARY OF THE INVENTION

The present invention provides structural DNA constructs which encode a phosphonate monoester hydrolase enzyme and which are useful for targeted plant cell lethality.

In accomplishing the foregoing, there is provided, in accordance with one aspect of the present invention, a recombinant, double-stranded DNA molecule comprising in sequence:

(a) a promoter which functions in plant cells to cause the production of an RNA sequence;
(b) a structural DNA sequence that causes the production of a phosphonate monoester hydrolase enzyme capable of hydrolyzing a compound having the structure:

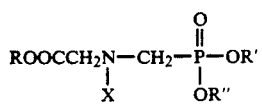

wherein R is hydrogen, a $C_1$-$C_4$alkyl, hydroxyalkyl or chloroalkyl, or a $C_2$-$C_6$ alkoxyalkyl group; R' is a $C_2$-$C_8$ alkyl, a $C_2$-$C_8$ hydroxyalkyl having from 1 to 6 hydroxyl groups, an arylalkyl or a substituted arylalkyl group; R" is hydrogen; and X is hydrogen, hydroxy, amino or $COCF_3$; as well as agronomically acceptable salts of such compounds; and (c) a 3' non-translated region which functions in plant cells to cause the addition of polyadenylate nucleotides to the 3' end of the RNA sequence, said promoter being heterologous with respect to the structural coding sequence.

In accordance with another aspect of the present invention, there is provided a method of producing genetically transformed plants which express a conditional lethal gene, comprising the steps of:

a) inserting into the genome of a plant cell a recombinant, double-stranded DNA molecule comprising
  (i) a promoter which functions in plant cells to cause the production of an RNA sequence;
  (ii) a structural DNA sequence that causes the production of a phosphonate monoester hydrolase enzyme capable of hydrolyzing a compound having the structure:

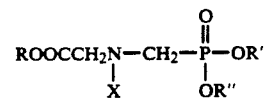

wherein R is hydrogen, a $C_1$-$C_4$alkyl, hydroxyalkyl or chloroalkyl, or a $C_2$-$C_6$ alkoxyalkyl group; R' is a $C_2$-$C_8$ alkyl, a $C_2$-$C_8$ hydroxyalkyl having from 1 to 6 hydroxyl groups, an arylalkyl or a substituted arylalkyl group; R" is hydrogen; and X is hydrogen, hydroxy, amino or $COCF_3$; as well as agronomically acceptable salts of such compounds;
  (iii) a 3' non-translated DNA sequence which functions in plant cells to stabilize and increase expression of the RNA sequence, said promoter being heterologous with respect to the structural coding sequence;
(b) obtaining transformed plant cells; and
(c) regenerating from the transformed plant cells genetically transformed plants which express the phosphonate monoester hydrolase.

There has also been provided, in accordance with another aspect of the present invention, bacterial and transformed plant cells that contain, respectively, DNA comprised of the above-mentioned elements (a), (b), and (c).

In accordance with yet another aspect of the present invention, differentiated plants are provided that express the phosphonate monoester hydrolase in a tissue critical for pollen development and which can be rendered male sterile by application of a protoxin having the structure:

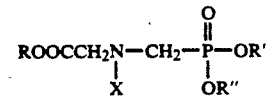

wherein R is hydrogen, a $C_1$-$C_4$alkyl, hydroxyalkyl or chloroalkyl, or a $C_2$-$C_6$ alkoxyalkyl group; R' is a $C_2$-$C_8$ alkyl, a $C_2$-$C_8$ hydroxyalkyl having from 1 to 6 hydroxyl groups, an arylalkyl or a substituted arylalkyl group; R" is hydrogen; and X is hydrogen, hydroxy, amino or $COCF_3$; as well as agronomically acceptable salts of such compounds.

BRIEF DESCRIPTION OF THE DRAWINGS

FIG. 2 shows the nucleotide sequence of the structural coding portion of the pehA (phosphonate monoester hydrolase) gene of PG2982. (Seq ID No: 1)

FIG. 5 shows the nucleotide sequence of the tapetal promoter 127a from tomato. (Seq ID No: 2)

DETAILED DESCRIPTION OF THE INVENTION

Figure 1:
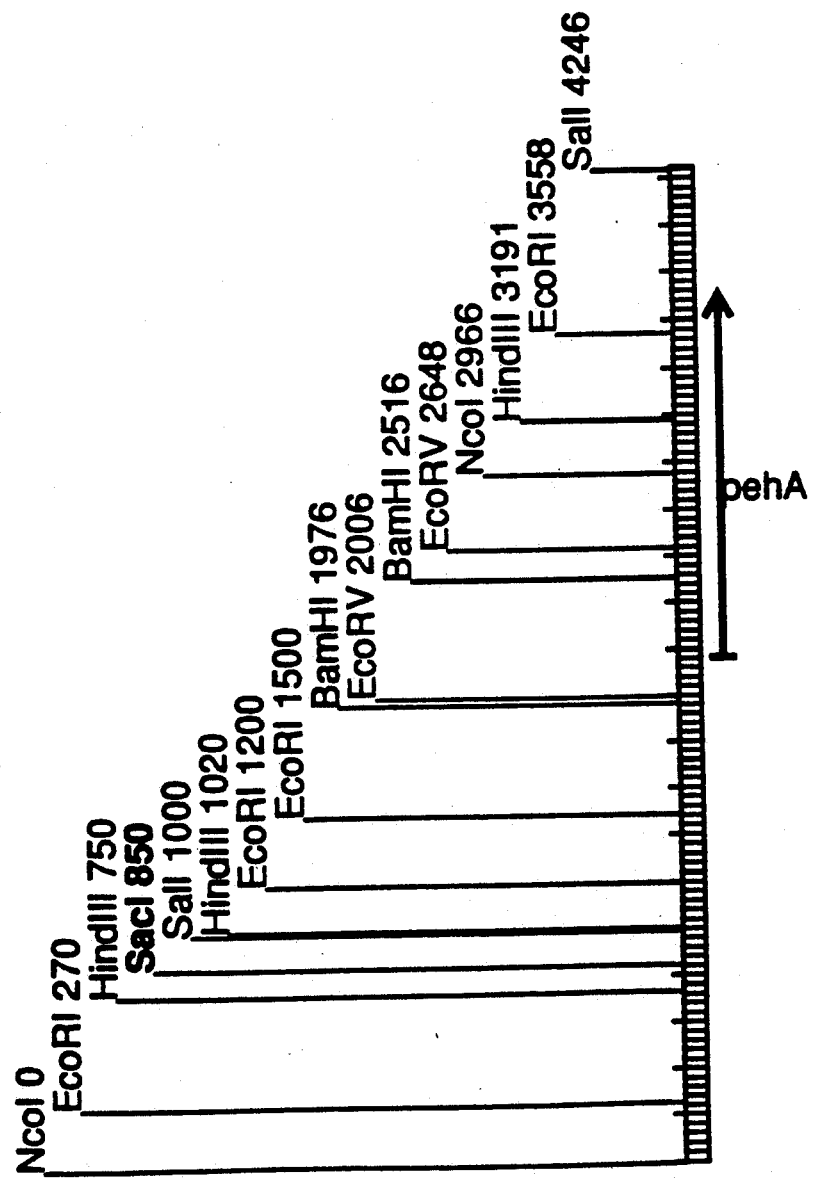
FIG. 1 shows an endonuclease restriction map for the genomic clone containing the pehA gene from isolate PG2982.

In the broadest sense, the present invention provides a means to selectively cause cellular lethality in plants using a heterologous dominant, conditionally lethal gene in combination with selected protoxin compounds. This methodology can be utilized in a variety of ways such as hybrid seed production, counter (negative) selectable markers and cell ablation. For brevity and clarity of explanation the following description will be focused on the use of the present invention in the context of hybrid seed production. Those skilled in the art will recognize that the present invention can be used in conjunction with virtually any selective cellular lethality by selectively expressing the subject phosphonate monoester hydrolase genes in the target cell type and subjecting said cell(s) to selected protoxin compounds.

In one exemplary embodiment, the invention comprises a process for the production of hybrid plants including monocotyledons such as rice, wheat, oats, barley, corn and the like as well as dicotylodons such as alfalfa, canola, carrot, cotton, oil seed rape, sugar beet, sunflower, soybean, tomato and the like. This process comprises applying a selected protoxin compound to a first plant species expressing the phosphonate monoester hydrolase in tissue of the anther cells critical for the development of the pollen or in the pollen itself in an amount that is effective to sterilize essentially all the male gametes of the plant while leaving a significant proportion of the female gametes capable of fertilization; causing the female gametes to be fertilized by pollen from a second plant; and thereafter harvesting the hybridized seeds.

The protoxin compounds used in the practice of the present invention have the formula

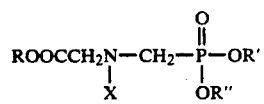

wherein R is hydrogen, a $C_1$-$C_4$ alkyl, hydroxyalkyl or chloroalkyl, or a $C_2$-$C_6$ alkoxyalkyl group; R' is a $C_2$-$C_8$ alkyl, a $C_2$-$C_8$ hydroxyalkyl having from 1 to 6 hydroxyl groups, an arylalkyl or a substituted arylalkyl group; R" is hydrogen; and X is hydrogen, hydroxy, amino or $COCF_3$; as well as agronomically acceptable salts of such compounds.

The compounds of the inventions are potentially amphoteric. Thus an acid such as hydrochloric acid can protonate the basic nitrogen atom or, if R or R' is hydrogen, a salt can be formed at one of these acidic hydrogens by reaction with a suitable base. Agronomically acceptable salts are salts in which the salt-forming moiety that reacts with the glyphosate derivative does not have any ecologically unacceptable consequences for the plant, the soil or the general environment. Acid that may form acceptable salts include hydrochloric acid, phosphoric acid and trifluoro acetic acid and based include the alkali metal hydroxides and those based on the "onium" ions such as ammonium, organoammonium, sulfonium, sulfoxonium, phosphonium and oxomium.

EVALUATION OF A GAMETOCIDE OR PROTOXIN

The critical tests for a prophytotoxin to be used in negative selection, cell ablation and as a gametocide are that the compound is non-phytotoxic per se but can be hydrolyzed into a phytotoxin by the phosphonate monoester hydrolase protein. The most general and specific method to determine if a protoxin is hydrolyzed to a toxic form of glyphosate is a HPLC assay. The compounds are dissolved at 100 mM concentration in a suitable buffer such as 10 mM TAPS, (N-Tris(hydroxymethyl)methyl-2-aminopropane sulfonic acid) pH 9.0. Triplicate samples (0.1 ml) of the compound are then diluted with 0.9 ml of 10 mM TAPS, pH 9.0 and with 0.9 ml 10 mM TAPS, pH 9.0 plus one unit (1 μmol/min) of enzyme. After 24 hour incubation at 25° C., the samples are injected onto a HPLC column for glyphosate analysis. The analysis for glyphosate by HPLC is well known and has been validated (Cowell et al., 1986). The protoxin and glyphosate are separated on an anion exchange column. the glyphosate is oxidized as it elutes in the presence of bleach and is then derivatized by o-pthaldehyde to a fluorescent derivative which can be quantitatively measured by a fluorescence monitor. If the protoxin in converted to glyphosate by a phosphonate monoester hydrolase, an increase in glyphosate will be observed in the presence of the enzyme as compared to the buffer control. As a second test, the protoxin is added to Arabidopsis tissue culture medium as described in Example 2 at 1 and 10 mM. Compounds which are stable, non-cytotoxic precursors of glyphosate will have no observable effect on Arabidopsis callus growth and shoot formation. Cytotoxic compounds or unstable precursors will result in callus necrosis or inhibition of shoot formation. For cell ablation, the protoxin must be able to translocate through the plant to reach the target tissue. Specifically for male sterility, the protoxin must be able to translocate to the developing anthers. One approach to studying the translocation is to apply radioactively labelled compound to a leaf. After two days, the plant is dissected into individual tissues and the amount of protoxin in each tissue determined. As an example, (3-$^{14}$C-) glycine, N-([hydroxy (2,3 dihydroxy propoxy) phosphonyl]methyl) was applied to tomato leaves. After two days, the plant was dissected and individual tissues frozen in liquid nitrogen and then freeze dried. The tissue samples were then combusted and the amount of radiolabelled compound in each tissue determined by scintillation counting.

The compound glycine, N-([hydroxy (2,3 dihydroxy propoxy) phosphonyl]methyl) is representative of the general class of phosphonate esters of glyphosate which meet the above criteria in that it is a substrate for the phosphonate monoester hydrolases, is relatively non-cytotoxic and translocates to developing anthers. Hereinafter the compound glycine, N-([hydroxy (2,3 dihydroxy propoxy) phosphonyl]methyl) will be referred to as glyceryl glyphosate.

PROMOTERS

Transcription of DNA into mRNA is regulated by a region of DNA referred to as the "promoter." The promoter region contains a sequence of bases that signals RNA polymerase to associate with the DNA strands as a template to make a corresponding complimentary strand of mRNA.

A number of promoters which are active in plant cells have been described in the literature. These include the nopaline synthase (NOS) and octopine synthase (OCS) promoters (which are carried on tumor-inducing plasmids of Agrobacterium tumefacians), the cauliflower mosaic virus (CaMV) 19S and 35S promoters, and the light-inducible promoter from the small subunit of ribulose-1,5-bis-phosphate carboxylase (ssRUBISCO, a very abundant plant polypeptide). All of these promoters have been used to create various types of DNA constructs which have been expressed in plants; see, e.g., PCT publication WO 84/02913.

Promoters which are known or are found to cause transcription of RNA in plant cells can be used in the present invention. Such promoters may be obtained from a variety of sources such as plants and plant viruses and include, but are not limited to, the enhanced CaMV35S promoter (Kay et al., 1987) and promoters isolated from plant genes such as ssRUBISCO genes. The particular promoter selected should preferably be capable of causing sufficient expression to result in the production of an effective amount of phosphonate monoester hydrolase enzyme to cause a lethal dose of protoxin to be converted into the cytotoxin.

The promoters utilized in the double-stranded DNA molecules are selected to confer specific expression in tissues where cell lethality is desired, such as in the tapetal cell layer of a plant anther to achieve male sterility in the case where the present invention is applied to the hybridization of plants. In order to achieve male sterility the preferred promoter should direct expression of the phosphonate monoester hydrolase in a tissue critical for pollen development such as the pollen itself, the tapetal cell layer of the anther, or other anther tissues. Also, the promoter should preferably not express in other plant tissues as to result in enough enzyme which will convert a damaging dose of protoxin to cytotoxin. A particularly preferred promoter is the p127a tapetal specific promoter described hereinafter in greater detail.

In addition to the p127a tapetal specific promoter, one skilled in the art can isolate additional alternative promoters by screening an anther cDNA library for anther-specific clones and then isolate the promoters in a manner similar to the way the p127a promoter was isolated. A number of anther-specific promoters have been described in the literature which may be fused to a conditional lethal gene to achieve conditional male sterility. An example of one such other promoter is the LAT52 promoter which has been cloned from a tomato library and can direct pollen-specific expression of the GUS gene in transgenic tomato and tobacco plants (Twell et al., 1989). The LAT52 promoter can be used to express the phosphonate monoester hydrolase gene which can then convert a protoxin into a cytotoxic product resulting in pollen abortion and male sterility.

Expression of other pollen specific cDNAs have been described in the literature. One skilled in the art can use these cDNAs to clone the promoter sequence and then use the pollen specific promoters to direct expression of the phosphonate monoester hydrolase gene in manner similar to that described for the p127A52 gene. Examples of these cDNAs include, but are not limited to, the promoter encoding a maize pollen specific cDNA described by Hanson et al. (1989) and the promoter to the P2 polygalacturonase cDNA from Oenothera organensis (Brown and Crouch, 1990). The chalcone falvonone isomerase B (chiB) gene directs anther specific expression in Petunia hybrida (van Tunen, et al., 1989). The promoter element has been identified and the sequence published (van Tunen, et al., 1988). Those skilled in the art can design primers to amplify the promoter from petunia DNA (using the polymerase claim reaction (PCR) techniques) and fuse the promoter to the phosphonate monoester hydrolase gene and transform many different plant species in order to express the phosphonate monoester hydrolase gene in anther tissues which will convert a lethal dose of protoxin into cytotoxin and result in male sterility. One skilled in the art will also recognize that the promoters described above can be used to isolate a homologous promoter from other plant species. The isolated homologous promoter is expected to be regulated more tightly in the species from which it is isolated.

In another aspect of the present invention any tissue-specific or developmental timing-specific promoter which can express an effective amount of phosphonate monoester hydrolase can be used in combination with the protoxin to achieve conditional lethality in the targeted tissue. The agamous promoter in tobacco (Yanofsky et al., 1990) is an example of a promoter which can be used in combination with the protoxin to prevent flower development in plants. Arresting floral development in crops such as sugar beet and potato would allow the biological resources normally used to develop reproductive structures to be redirected to the economic structures such as the beet or tuber, respectively. A promoter which would express the phosphonate monoester hydrolase in young flower buds in mums would allow the protoxin to be used to "pinch" (arrest) the first flowers so that a larger, more uniform bloom would be obtained in the fall.

The RNA produced by a DNA construct of the present invention also contains a 5' non-translated leader sequence. This sequence can be derived from the promoter selected to express the gene, and can be specifically modified so as to increase translation of the mRNA. The 5' non-translated regions can also be obtained from viral RNAs, from suitable eukaryotic genes, or from a synthetic gene sequence. The present invention is not limited to constructs, as presented in the following examples, wherein the non-translated region is derived from the 5' non-translated sequence that accompanies the promoter sequence. Rather, the non-translated leader sequence can be derived from an unrelated promoter or coding sequence as discussed above.

The 3' non-translated region of the chimeric plant gene contains a polyadenylation signal which functions in plants to cause the addition of adenylate nucleotides to the 3' end of the RNA. Examples of preferred 3' regions are (1) the 3' transcribed, non-translated regions containing the polyadenylate signal of Agrobacterium tumor-inducing (Ti) plasmid genes, such as the nopaline synthase (NOS) gene, and (2) plant genes like the soybean 7s storage protein genes and the pea small subunit of the ribulose-1,5-bisphosphate carboxylase (ssRUBISCO) E9 gene.

The DNA constructs of the present invention also contain a structural coding sequence in double-stranded DNA form, which encodes phosphonate monoester hydrolase enzyme that hydrolyzes a wide range of phosphonate esters. An example of preferred phosphonate ester protoxins are the phosphonate esters of glyphosate.

THE PHOSPHONATE MONOESTER HYDROLASE REACTION

The enzyme phosphonate monoester hydrolase (PEH) of the present invention catalyzes the cleavage of phophonate esters into the free phosphonate and an alcohol. The enzyme was first identified by its ability to hydrolyze the glyceryl glyphosate into glycerol and glyphosate. The enzyme has since been shown to hydrolyze other protoxin compounds employed in the practice of the present invention as well as numerous other phosphonate monoesters including colorimetric substrates.

The enzymatic reaction can be assayed using labelled (3-$^{14}$C-) glyceryl glyphosate as a substrate and following the conversion to (3-$^{14}$C-)glyphosate as a product using a high pressure liquid chromatography system with a radioactive detector. This assay is the most specific for the phosphonate monoester hydrolase enzymes useful for conditional cell lethality. An enzyme assay consists of 40,000 cpm of labelled (3-$^{14}$C-) glyceryl glyphosate (obtained from NEN Biochemicals), the PEH sample in buffer and buffer to 100 µl final volume. The assay buffer is 10 mM Bis-Tris propane, pH 9.0, plus 100 mM KCl. The reaction is run for 1 hour at 30° C. and then stopped by the addition of 100 µl "quench" which is 100 mM sodium acetate, pH 5.5, in ethanol. The denatured protein is then spun down at 10,000 rpm in a microfuge and the supernatant transferred to an HPLC injection vial. A 100 µl aliquot is then injected onto an Synchropac AX100 anion exchange column 4.6×250 mm) pre-equilibrated in 65 mM potassium phosphate buffer, pH 5.5. The radioactive compounds are eluted isocratically for 15 min at 1 ml/min. The radioactivity of the peaks is measured and integrated by a post-column detector. Typically, the substrate elutes at 4.9 min and the product, glyphosate, at 9.7 min providing baseline separation. The radioactive glyceryl glyphosate has been found to be unstable where stored at −20° C. over a period of 3 months and must first be purified to remove glyphosate and any other contaminant. Alternatively, blank reactions can be included to determine the preexisting glyphosate contamination.

A second phosphonate monoester hydrolase activity assay specific to the hydrolases useful for conditional cell lethality measures the glycerol released from glyceryl glyphosate by coupling the reaction to glycerol dehydrogenase. The assay includes 0.5 ml phosphonate monoester hydrolase sample in buffer and 0.5 ml GDH reaction mix consisting of 1.51 mM β-NAD, 0.8 U NADH:dye oxidoreductase (Boehringer Mannheim), 2 U glycerol dehydrogenase (Boehringer Mannheim), 300 mM NH$_4$SO$_4$, 50 mM Bis-Tris propane, pH 09.0, 0.03% Triton X-100 and 0.08 mM p-Iodonitrotetrazolium Violet (INT). The reaction proceeds with the formation of a red color which is measured at 492 nm in a spectrophotometer.

A more convenient but less specific assay is the enzymatic hydrolysis of p-Nitrophenyl phenylphosphonate (pNPP). A typical assay includes 4 mM pNPP in buffer, the PEH sample in buffer, and buffer to 1 ml. The preferred buffer is 10 mM Bis-Tris propane, pH 9.0, plus 100 mM KCl. The reaction is initiated by the addition of the PEH sample and followed by continuous spectrophotometric measurement at 400 nm. Although easy to use, the assay is non-specific since pNPP is a substrate for several common enzymes including 5'-nucleotide phosphodiesterase (Kelly and Butler, 1975).

The activity of the enzyme can also be stained in situ after native polyacrylamide gel electrophoresis (PAGE). Native PAGE gels were prepared as described (Hames, 1985) using the Tris-Glycine discontinuous buffer system of Davis, 1964. The proteins were separated on a 7.5% acrylamide gel at 12 mA overnight with cooling to 4° C. using a Hoeffer model SE600 vertical slab gel apparatus. Alternatively, proteins were also separated on a Phastsystem using 10–15% gradient native PAGE gels as described (Pharmacia Phastsystem Owner's Manual. 1987. Pharmacia/LKB, Princeton, N.J.). After electrophoresis, the gels were stained for activity by pouring a thin layer of 10 mM Bis-Tris propane, pH 9.0, 100 mM KCl, 25 mM β-naphthyl phenyl phosphonate and 1% Fast Blue. Activity bands usually appeared within two minutes at which time the reaction was stopped by rinsing the gel in H$_2$O.

The expression of phosphonate monoester hydrolase activity was also detected using a 5-bromo-4-chloroindolyl phenyl phosphonate (XPP) histochemical assay. Expression in *E. coli* was detected by simply including 0.1% XPP in the medium. Expression of the pehA gene resulted in blue colonies which were viable. Plant cells were screened for pehA expression by soaking the tissue in 100 mM Bis-Tris propane, pH 9.0, 0.005M K$_3$[Fe(CN)$_6$], 0.005M K$_4$[Fe(CN)$_6$], 5 mM EDTA 0.1% Triton X-100 and 0.025% XPP. Additionally, thin sections of plant tissues were stained for pehA activity by soaking the sections in the above solution except 1% XPP was included in the buffer. After staining, the tissue was fixed in FAA (40% ethanol, 5% glacial acetic acid and 10% formalin) and dehydrated with a graded alcohol series.

ISOLATION OF AN EFFICIENT PROTOXIN-TO-GLYPHOSATE (CYTOTOXIN) DEGRADING BACTERIUM

Bacteria capable of degrading glyphosate are known (Hallas et al., 1988; Malik et al., 1989; and Moore et al., 1983; Heitkamp et al., 1990). Five of these bacteria (PG2482, LBAA, T10, T12 and CP4) and four strains of *E. coli* were screened for the rapid degradation of glyceryl glyphosate into inorganic phosphate. The bacteria were inoculated into 2 ml Dworkin-Foster (DF) minimal medium containing glucose, sodium gluconate and potassium citrate (each 0.1%) as carbon source and containing 0.2 mM glyceryl glyphosate as a phosphate source. The Dworkin-Foster minimal medium was made by combining 1 liter sterile $H_2O$ with 1 ml each of A, B, C, E and F, 10 ml D, C-sources to final concentration of 0.1% each and P-source to 0.2 mM.

| | | |
|---|---|---|
| A. D-F Salts | (1000X stock; per 100 ml autoclaved) | |
| $H_3BO_3$ | | 1 mg |

| | | |
|---|---|---|
| MnSO$_4$.7H$_2$O | | 1 mg |
| ZnSO$_4$.7H$_2$O | | 12.5 mg |
| CuSO$_4$.5H$_2$O | | 8 mg |
| NaMoO$_3$.3H$_2$O | | 1.7 mg |
| B. FeSO$_4$ Stock | (1000X stock; per 100 | ml autoclaved) |
| FeSO$_4$.7H$_2$O | | 0.1 g |
| C. MgSO$_4$ Stock | (1000X stock; per 100 | ml autoclaved) |
| MgSO$_4$.7H$_2$O | | 20 g |
| D. (NH$_4$)$_2$SO$_4$ Stock | (1000X stock; per 100 | ml autoclaved) |
| (NH$_4$)$_2$SO$_4$ Stock | | 20 g |
| E. Thiamine Stock | (1000X stock; per 100 | ml filter sterilized) |
| Thiamine.HCl | | 500 mg |
| F. Yeast Extract | (1000X stock; per 100 | ml autoclaved) |
| Difco Yeast Extract | | 10 g |

Bacteria which grew in this medium using glyceryl glyphosate as a sole phosphate source had the ability to cleave both the ester and the phosphonate bond to release the free phosphate. For these bacteria to be useful in the present invention, the first step in the mineralization of glyceryl glyphosate needed is the hydrolysis of the phosphonate ester. Each of the three bacteria which utilized glyceryl glyphosate as a phosphate source were then assayed for a phosphonate monoester hydrolase activity using an in vivo (3-$^{14}$C-) glyceryl glyphosate assay. A 150 ml culture of each bacteria was grown in DF minimal medium with 0.2 mM HK$_2$PO$_4$ as a phosphate source in a 500 ml flask, 30° C., with shaking. The bacteria were pelleted by centrifugation at 5,000× g for 10 min and resuspended at 10 mg fresh weight/ml. An assay mix included 50 μl cells plus 10 μl (3-$^{14}$C-) glyceryl glyphosate (10,000 cpm/μl) and kept at 30° C. with shaking. After a three hour incubation period, the cells were pelleted in a microfuge and the supernatant injected onto an HPLC anion exchange column and glyphosate analyzed as described above. The pellet was washed twice with 1 ml 10 mM HEPES, pH 7.0, and resuspended in 25 μl buffer. The cells were lysed with 25 μl quench and the debris pelleted in a microfuge. The pellet extract was then analyzed for glyphosate product as described above. Glyphosate was found in the pellet extracts of these three bacteria indicating the presence of a phosphonate monoester hydrolase activity in these organisms. An in vitro radioactive assay was also performed on some of the bacteria which further indicated that they contained a phosphonate monoester hydrolase. A summary is presented in the following table (Table I):

TABLE I

| Bacterial Strain | Glyceryl Glyphosate as Phosphate Source | In vivo Hydrolysis of Glyceryl Glyphosate into Glyphosate | Hydrolysis of Glyceryl Glyphosate into Glyphosate in Crude Extracts |
|---|---|---|---|
| PG2982 | Yes | Yes | Yes |
| LBAA | Yes | Yes | Yes |
| T10 | Yes | Yes | No |
| T12 | No | — | Yes |
| CP4 | No | — | — |
| E. coli[1] | No | No | No |

[1]MM294, JM101, JM101/MPU+, SR200/MPU+

CLONING OF THE PG2982 PHOSPHONATE MONOESTER HYDROLASE pehA GENE

For clarity and brevity of disclosure, the following description of the isolation of genes encoding the subject phosphonate monoester hydrolase enzymes is directed to the isolation of such a gene from *Pseudomonas caryophilli* PG2982. (NCIMB #12533). Those skilled in the art will recognize that the same or a similar strategy can be utilized to isolate such genes from other microbial isolates. The strategy for cloning the enzyme was to purify it to homogeneity, isolate and sequence tryptic fragments, design oligos to the tryptic fragments to use in PCR reactions to obtain a fragment of the pehA gene and to use that fragment as a probe to isolate the complete gene from a cosmid library.

To obtain enzyme for purification, five 10 liter fermentations of PG2982 cells were carried out in Dworskin-Foster minimal medium. At each step of the purification, activity assays were performed using the glycerol release assay described above except towards the end of the purification when the pNPP assay was used after confirming that contaminating activities had been removed by purification. The cells (200 g) were harvested by centrifugation and resuspended in 1 l buffer I, 100 mM Tris, pH 8.0, 100 mM KCl, 2 mM DTT. A lysate was made by passing the cells through a Mantin-Gaulin Press three times. The cell debris was pelleted by centrifugation and the supernatant collected. Protamine sulfate was added to the crude extract to 0.2% and then the precipitate was pelleted. The enzyme activity was found in the pellet and the supernatant. Additional protamine sulfate was added to the supernatant to 0.4% total concentration and the nucleic acids and remaining PEH activity was precipitated. The two protamine sulfate pellets were combined, brought to 0.5M KCl in buffer and resuspended with stirring with a magnetic stir bar. The mixture was centrifuged and the soluble PEH activity removed in the super. A substantial amount of activity remained with the nucleic acids which was extracted a second time as above. The second protamine sulfate extract was saved for a week and purified in the same manner as the first extract and then combined with the first purification where indicated below. The protamine sulfate extract was then brought to 50% ammonium sulfate and the precipitated protein was collected by centrifugation. The ammonium sulfate pellet was resuspended in 100 ml buffer I and dialyzed against two 4 l changes of 50 mM Tris, pH 8.0, 2 mM DTT overnight. All procedures were carried out at 4° C. The dialyzed ammonium sulfate extract was loaded on a Q-sepharose fast flow anion exchange column (4×40 cm) equilibrated in dialysis buffer. The PEH protein was eluted towards the end of a 2 l, gradient of 0–500 mM KCl in dialysis buffer. The middle fractions containing activity were pooled and PEH precipitated with 50% ammonium sulfate. The ammonium sulfate pellet was then loaded on a 2.6×100 cm sephacryl S-200 gel filtration column equilibrated in 10 mM Tris, pH 8.0, 50 mM KCl and 5 ml fractions collected. The PEH activity eluted just after the void volume and the fractions with the highest specific activity were pooled and loaded on a FPLC MonoQ anion exchange column. The PEH activity was eluted with a 30 ml 0–500 mM KCl gradient in 10 mM Tris, pH 8.5. The fractions with the highest activity were pooled and rechromatographed on the MonoQ column using a 0–500 mM KCl gradient in 60 ml of 10 mM Tris, pH 8.5. Fractions containing the highest activity were again pooled. The pooled activity was then further purified using Native PAGE as described above but using a preparative 4 mm×8 cm resolving gel. The PEH protein was assayed by soaking the gel in a solution of 4 mM pNPP in 100 mM Tris, pH 8.5, 100 mM KCl. The incubation was stopped by rinsing the gel with H₂O as soon as a yellow band appeared. The activity band was excised, one fifth stored at −20° C. and later used in rabbit polyclonal antibody production while the remaining PEH protein was electroeluted using a BioRad Mini Protean II electroeluter in 10 mM Tris, 20 mM glycine, pH 8.5. The PEH protein was then brought to 40% ammonium sulfate using a saturated stock solution and loaded on a FPLC alkyl superose HR5/5 column equilibrated in 10 mM TAPS, pH 9.0, 40% (NH₄)₂SO₄. The PEH activity eluted in the middle of a 25 ml gradient of 40-0% (NH₄)₂SO₄. The recovery was 800 μg. Although a single band was evident by native PAGE 10-15% phastgels, two bands, a 66 kD and a 59 kD polypeptide, were apparent after SDS PAGE on a 10-15% phastgel and silver staining using standard procedures (Phastgel Owners Manual). In a final attempt to separate these two bands by column chromatography, 600 ug of the pure PEH protein were injected on a C4 column equilibrated in H₂O and then eluted with a 0-100% acetonitrile+0.1% trifluoroacetic acid gradient collecting fractions. Again the protein eluted as a single peak. Since only a single peak of protein eluted from the alkyl superose and C4 column and a single band was evident on a native PAGE gel, both bands on the SDS PAGE gel were likely PEH polypeptides.

Tryptic maps were obtained for both the 66 kD and the 59 kD polypeptide to compare their similarity and to obtain tryptic fragment sequences necessary to clone the gene. The 600 μg of protein recovered from the C4 column step was dried down in a rotovap and dissolved in 200 μl of 0.5M Tris, pH 8.0 with 6M guanidine hydrochloride for full reduction and carboxymethylation. The solution was brought to 10 mM DTT by adding a 1M stock and incubated for two hours at 37° C. Iodoacetic acid was then added to 20 mM and incubated overnight. The sample was then dialyzed against 50 mM Tris, pH 8.0. The dialyzed protein was then denatured by addition of SDS to 0.1% and boiled 5 min. The 66 and 59 kD polypeptides were separated from each other by electrophoresis on a 3-17% acrylamide gradient SDS PAGE mini gel (premade by Jule Inc.) run at 30 mA. The two polypeptides were visualized by a brief 15 min staining in 0.3% coomassie blue in H₂O. The faintly stained bands were excised and electroeluted using a BioRad Mini Protean II electroeluter in 25 mM Tris, 192 mM glycine and 0.1% SDS. The eluted polypeptides were dialyzed against H₂O for four hours and each precipitated with 5 vol acetone, resuspended in 0.1M ammonium bicarbonate, pH 8.1. NaOH was added to 0.1M and the samples heated at 40° C. for 5 min and then desalted into 0.1M ammonium bicarbonate, pH 8.1 using a Sephadex G-25 column. A 1 μl sample of each polypeptide was run on a 10-15% SDS PAGE phastgel to confirm the two polypeptides were cleanly separated. The polypeptides were then digested with trypsin 1:25 wt/wt overnight. One-tenth of each tryptic digest was separated on a C8 column using an 0 to 60% acetonitrile gradient in 30 ml to obtain a tryptic map for comparison. The tryptic maps for both polypeptides were nearly identical suggesting they were encoded by the same gene. After confirming good digestion, the remaining digest was fractionated on the C8 column with a 0-60% acetonitrile gradient over 60 ml collecting individual peaks as they eluted. Peaks with good separation from the remaining fragments were submitted for amino acid sequencing. Five tryptic sequences were obtained from the 66 kD polypeptide and one from the 59 kD polypeptide (Table II). The N-terminal amino acid sequence was also obtained using purified PEH protein after the preparative native PAGE (Table II). Even though this preparation was a mixture of the top and bottom band, a single sequence was obtained suggesting the two polypeptides had the same N-terminal sequence.

TABLE II

| Fragment | Sequence |
|---|---|
| N-terminus | XRKNVLLIVVDQ(C)RADFIPHL MRAEGREPFLXXPN (Seq ID No: 3) |
| T32 | XXGAFEANX(Q) (Seq ID No: 4) |
| T20 | EDIWLPEGEHSVPGATDKPSR (Seq ID No: 5) |
| T37 | AYLDETGQ (Seq ID No: 6) |
| T25 | AAGQDEAIN-E (Seq ID No: 7) |
| B30 | XAGQD(C)/EAINXE (Seq ID NO: 8) |

\* A ( ) indicates a tenous determination
\*\* The T and B indicate sequence from 65 and 59 kD polypeptide, respectively.
\*\*\* The numbers indicate the fraction number of the purified fragment.

In this and all amino acid sequences to follow, the standard single letter nomenclature is used. All peptide structures represented in the following description are shown in conventional format wherein the amino group at the N-terminus appears to the left and the carboxyl group at the C-terminus at the right. Likewise, amino acid nomenclature for the naturally occurring amino acids found in protein is as follows: alanine (Ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (Lys;K), methionine (Met;M), phenylalanine (Phe;F), proline (Pro;P), serine (Ser;S), threonine (Thr;T), tryptophan (Trp;W), tyrosine (Tyr;Y), and valine (Val;V). An "X" is used when the amino acid residue is unknown and parentheses designate that an unambiguous assignment is not possible and the amino acid designation within the parentheses is the most probable estimate based on known information.

The next step in the cloning strategy was to use the PCR reaction technique to amplify a segment of the gene between two of the tryptic fragments. This gene segment would then be used as a probe against a genomic library to clone out the entire coding sequence. Five PCR primers (Table III) were designed using the sequence of the N-terminal amino acids and tryptic fragments T20 and T37.

TABLE III

| Primer | Sequence |
|---|---|
| N-terminus | ATC GTA/G GAT CAG TGC CGC GCA GAT TTC ATC CCG CAT CTA ATG (Seq ID No: 9) |
| T20A | GAA/G GAC/T ATC/T TGG CTN CC (Seq ID No: 10) |
| T20B | GAA/G GAC/T ATC/T TGG TTA/G CC (Seq ID No: 11) |
| T20C | GAA/G GAC/T ATC/T TGG CTG/G CCC/G GAA/G GGC/T CA (Seq ID No: 12) |

TABLE III-continued

| Primer | Sequence |
|---|---|
| T37B | TGG/A CCG/C GTC/T TCA/G TC (Seq ID No: 13) |

* A slash indicates a mixture of two nucleotides at that position.

The primers T20 A and B were designed from the same tryptic sequence but synthesized separately to minimize the degeneracy and then pooled at a ratio of 2:1, respectively, prior to PCR amplification. T20C and T37B are antisense primers to the tryptic sequence. The PCR primers were synthesized by Midland Scientific and the PG2982 genomic DNA template was prepared as follows. The cell pellet from a 100 ml L-broth (Miller, 1972) late log phase PG2982 culture was resuspended in 10 ml of Solution I (Birnboim and Doly, 1979). SDS was added to 1% wt/vol and the suspension was subjected to three freeze-thaw cycles, each consisting of immersion in dry ice for 15 min and in water at 70° C. for 10 minutes. The lysate was then extracted four times with equal volumes of phenol:chloroform (1:1; phenol saturated with TE) (TE=10 mM Tris, pH 8.0, 1 mM EDTA) and the phases separated by centrifugation (1500 g; 10 min). The DNA was precipitated from the top phase using 2 vol ethanol and collected by brief centrifugation (8000 g; 5 min). The DNA pellet was resuspended in 5 ml TE and dialyzed for 16 h at 4° C. against 2 l of TE. The DNA was ready to be used as a PCR template and for making a library as described below.

The PCR experiment was designed so that each sense primer was in combination with each antisense primer and each primer was also included in a reaction alone as a control. The PCR reactions were performed as recommended by the manufacturer (Perkin Elmer Cetus). A 100 μl reaction contained 50 pmol each of a 5' and 3' primer, 1 μg PG2982 genomic DNA, 2.5 U Taq polymerase and 0.25 mM each of the four deoxynucleotide triphosphates. The reaction was run for 25 cycles with a 1 min, 94° C. denaturation step, a 2 min, 40° C. annealing step, and a 3 min, 72° C. extension step. A number of bands were amplified in each experimental and control reaction. However, after eliminating the bands which occurred in the control and experimental reactions as possible pehA products, only a single highly amplified band remained in each experimental reaction. Table IV lists the results from the PCR experiment.

TABLE IV

| Primer Set | Unique Amplified Product size (bp) |
|---|---|
| Nterm-T20C | 450 |
| T20A/B-T37B | 450 |
| Nterm-T37B | 900 |

If the T20 primers are 450 bp from the N-terminus and the T37B primer is 450 bp from the T20 primers, then an independent prediction requires the T37B primer to be 900 bp from the N-terminus which is the observed result above. This result provides confidence that a pehA gene segment has been amplified and not an artifact.

To further confirm the identity of the amplified products, the T20A/B-T37B amplified gene segment was sequenced according to the standard double stranded DNA sequencing protocol of the Sequenase Ver. 2.0 kit using the manganese buffer to obtain sequence adjacent to the primer. The gene segment was purified by running 20 ul of the amplified reaction out on a 2% agarose gel in TEA buffer. The 450 bp band was identified by ethidium bromide staining and sliced out of the gel. The DNA was eluted by freezing the gel slice in 30 ul TE at −70° C. and then spinning the slice at 10,000 g for 20 min to force the DNA and buffer out of the gel. The liquid above the gel was then brought to 200 ul by addition of TE, extracted with phenol:chloroform, and the DNA precipitated with sodium acetate and ethanol. The precipitated DNA was collected by centrifugation, washed with 70% ethanol and resuspended in 20 ul TE buffer. The DNA concentration was determined to be about 16 ng/ul. For sequencing, 5 ul of double stranded DNA was denatured by the addition of 5 ul of TE, 10 ul H2O, and 2 ul 2M NaOH. After 5 min, the solution was neutralized by addition of 3 ul of 3M potassium acetate, pH 4.8 and 7 ul H2O. The denatured DNA was then precipitated with the addition of 75 ul of ethanol. The denatured DNA pellet was redissolved in 7 ul H2O and 1 ul of the T20A/B primers (1.2 pmol) and 2 ul manganese annealing buffer were added and the primers and template annealed at 65° C. for 5 min followed by slow cooling to room temperature. Nucleotides (dG labeling mix), DTT, $^{35}$S-dATP, and Sequenase 2.0 were added and the elongation reaction run 4 min before initiating the four 5 min termination reactions with the ddNTP mixtures. The sequencing products were separated on a 7% acrylamide gel in TBE buffer and the sequence read from a overnight film exposure of the sequencing gel. The T20 primers were designed using the DIWLP amino acid sequence at the 5' end of the tryptic fragment. By using the T20 primers, the deduced amino acid condons from the DNA sequence of the PCR product can be compared to the amino acids observed towards the C-terminal end of the tryptic fragment. If the T20A/B-T37B PCR product was an authentic peh gene segment, a portion of the deduced amino acid sequence should match the observed T20 tryptic fragment amino acids. Table V below lists the deduced amino acid sequence versus the amino acid sequence of the T20 tryptic fragment.

TABLE V

| Source | Sequence |
|---|---|
| Deduced Amino Acids from PCR Product | HSVPGATDKXXR ... (Seq ID No: 14) |
| T20 Tryptic Fragment Sequence | EDIWLPEGEHS VPGATDKPSR (Seq ID No: 15) |

The deduced amino acids of the PCR product did overlap the C-terminal end of the T20 tryptic sequence providing complete confidence that the PCR product is a pehA gene segment.

To obtain a full length pehA gene, the T20A/B-T37B 450 bp PCR product was used as a probe to a PG2982 cosmid library. The PG2982 genomic library was constructed from partially restricted genomic DNA (described above) prepared as follows: Three 100 μg aliquot samples of PG2982 DNA were treated for 1 hour at 37° C. with restriction endonuclease HindIII at rates of 4,2 and 1 enzyme unit/ug DNA, respectively. The DNA samples were pooled, made 0.25 mM with EDTA and extracted with equal volume of phenol:chloroform.

Following the addition of sodium acetate and ethanol, the DNA was precipitated with two volumes of ethanol and pelleted by centrifugation (12000 g; 10 min). The dried DNA pellet was resuspended in 500 μl TE and layered on a 10–40% sucrose gradient (in 5% increments of 5.5 ml each) in 0.5M NaCl, 50 mM Tris, pH 8.0 and 5 mM EDTA. Following centrifugation for 20 h at 26,000 rpm in a SW28 rotor, the tubes were punctured and 1 ml fractions collected. Samples (15 μl) of each third fraction were run on 0.8% agarose gel and the size of the DNA determined by comparison with linearized lambda DNA and HindIII-digested lambda DNA standards. Fractions containing DNA of 25–35 kb fragments were pooled, desalted on Amicon 10 columns (7000 rpm; 20° C.; 45 minutes) and concentrated by precipitation. This procedure typically yielded 50 μg of PG2982 DNA of the required size.

The partially restricted DNA was then ligated into a cosmid vector, pHC79 (Hohn and Collins, 1980). Plasmid pHC79 was restricted with HindIII and phosphatase digested using calf intestinal phosphatase (Maniatis et al., 1982). The phosphatase-treated vector was purified by phenol:chloroform extraction and precipitated with sodium acetate and ethanol. PG2982 DNA (3.75 μg) was ligated to the phosphatased vector (1.6 μg) using T4 DNA ligase (400 U) (Boehringer-Mannheim) in 22 μl ligation buffer (25 mM Tris, pH 8.0,10 mM $MgCl_2$, 10 mM dithiothreitol and 0.2 mM spermidine). The ligated cosmid library (4 μl) was packaged into lambda phage particles using the standard protocol with the Gigapack Gold kit (Stratagene).

The PG2982 library was then screened using colony hybridization to the T20A/B-T37B PCR product. A culture of E. coli HB101 was grown overnight in L-broth with 0.2% maltose added and then infected with 50 μl packaged library for 2 h ending with the addition of 15 μl chloroform. A 10 μl aliquot of infected cells was plated on LB plates with 200 μg/ml ampicillin to check titre. The library was then plated using 300 colony forming units per plate on LB plates with 200 μg/ml ampicillin and incubated overnight at 37° C. When the colonies were 0.2 mm in diameter, the colonies were replicated onto duplicate nylon membranes (Magna 66) using Repliplate pads (FMC) and incubated overlaying fresh LB+200 μg/ml ampicillin plates until the colonies were again 0.2 mM in diameter. The filters with colonies were transferred to Whatman 3MM saturated with 10% SDS for 3 min, then 0.5M NaOH for 5 min and finally to paper saturated with 0.5M sodium acetate for 5 min. The filters were then rinsed in 2XSSC (0.15M NaCl, 0.015M sodium citrate, pH 7.0), air dried 30 min and baked at 80° C. for 1 h. The baked filters were wetted in 2XSSC for 5 min and prewashed in 6XSSC 0.5% SDS and 1 mM EDTA for 30 min at 50° C. After washing excess debris was removed with a chemwipe wetted in prewash solution. The filters were then treated overnight at 68° C. in a prehybridization solution of 6XSSC, 0.5% SDS, 100 μg/ml sheared salmon sperm DNA, 50 μg/ml tRNA and 5X Denhardt's solution (5X is 0.1% ficoll Type 400, 0.1% polyvinylpyrrolidone and 0.1% bovine serum albumin) using 8 ml/filter. The prehybridization solution was poured off and replaced with hybridization solution; 6XSSC and 0.5% SDS, using 5 ml/filter. The $^{32}P$ labeled 450 bp T20A/B-T37B PCR product was added as a probe at $2 \times 10^6$ cpm/filter. The probe was labeled just prior to its use by random oligo priming. The labelled probe was purified on a G-25 spin column. Hybridization was performed for 14 h at 68° C. and then the filters were washed 2× at 23° C. with 6XSSC, 0.2% SDS for 15 min and 1× at 68° C. and then exposed to film.

Colonies which hybridized to the probe on each of the duplicate filters were likely to contain the pehA gene on a genomic fragment. To confirm this hypothesis the colonies were further screened using a colony PCR technique. A PCR mix containing per 100 μl, 1× PCR buffer, 50 pmol of N-terminal primer, 50 pmol of T37B primer, 0.25 mM each dNTP and 2.5 U Taq polymerase was aliqouted to PCR tubes and part of the bacterial colony picked and dispersed in the reaction mixture. The PCR reaction was then run using a 1 min, 94° C. denaturation step (which also lysed the bacteria), a 3 min, 50° C. annealing step and a 2 min, 72° C. extension step. The reactions were then analyzed for the presence of the 900 bp product consistent with previous PCR results to confirm an authentic pehA genomic clone. Three colonies were identified by colony hybridization and were confirmed to contain a cosmid with the pehA gene by PCR.

Since the cosmids were 30–40 kb and the pehA gene was predicted to be about 1600 bp based on the estimated molecular weight of the pure protein, the pehA gene needed to be subcloned from one of the cosmids. Cosmid DNA was prepared using a rapid alkaline lysis method. A 2 ml culture of the recombinant E. coli was grown to saturation and 1.5 ml transferred to a microfuge tube. The cells were pelleted by brief centrifugation in a microfuge and resuspended in 200 μl 25 mM Tris, pH 8.0, 50 mM glucose and 10 mM EDTA. The bacteria were then lysed by the addition of 400 μl freshly made 0.2N NaOH with 1% SDS and held on ice 5 min. Then, 300 μl of 3M potassium and 5M acetate was added, mixed thoroughly but gently, and cell debris precipitated by centrifugation. The supernatant was extracted with an equal volume of phenol:chloroform (1:1; phenol was saturated with TE) and the phases separated by centrifugation. The aqueous phase was then combined with ⅓ volume isopropanol and the nucleic acids precipitated at room temp. The DNA pellet was washed once with 70% ethanol and then allowed to dry before resuspending in 50 μl TE. The cosmid was then digested with a number of restriction enzymes including BglII, BamHI, ClaI, NcoI, HindIII and EcoRI and analyzed by southern blot. The restricted DNA was separated on a 0.8% agarose gel in TAE (0.04M Tris-acetate, 0.001M EDTA). The DNA was then partially depurinated by soaking the gel in 0.25M HCl for 10 min, denatured in 0.5M NaOH with 1M NaCl for 30 min, and neutralized in 0.5M Tris, pH 7.5 with 1.5M NaCl for 30 min. The DNA was then vacuum blotted onto a nylon membrane in neutralizing solution (Millipore Vacuum Blotter) and UV cross-linked to the membrane by a 3 min exposure to a short-wave UV lamp. The southern blot was then treated in 30 ml prehybridizing solution; 6XSSC, 0.5% SDS, 100 μg/ml sheared salmon sperm DNA, 5× Denhardt's, for 1 h at 68° C. The blot was then hybridized overnight at 68° C. in 15 ml 6XSSC, 0.5% SDS, 100 μg/ml salmon sperm DNA and $1 \times 10^6$ cpm/ml of $^{32}P$-labeled probe. The probe was the 0.88 kb Nterm-T37B PCR product (Table II) labelled with $^{32}P$ using random oligo priming as described above. After hybridization, the blot was washed 2×15 min in 2XSSC, 0.1% SDS at 23° C. then 1×15 min in 2X SSC, 0.5% SDS at 68° C. Each digest yielded a single band hybridizing to the probe except BamHI which yielded a large >10 kb band and a small approximately 500 bp piece. The two bands in the BamHI digest indicate a BamHI site in the region between the N-terminus and tryptic 37 sequences. The NcoI and the HindIII digests yielded a 3 kb and a 2.2 kb band, respectively, which hybridized to the probe. To isolate these fragments, the cosmid was again digested with these two enzymes, the fragments separated on a 1.0% agarose gel and the bands identified using DNA size markers in adjacent lanes. The bands were purified from the gel using Gene Clean kit and the NcoI fragment was ligated into pMON7258 (a pUC118 derivative) giving pMON9418 and the HindIII fragment was ligated into Bluescript pSK (Clonetech) giving pMON9419. To confirm the correct fragment had been subcloned, colonies transformed with the above ligations which contained an insert were tested for the Nterm to T37B segment using the PCR colony screen. A single colony was picked which contained the correct insert for each fragment. The inserts in pMON9418 and pMON9419 were mapped using common restriction enzymes and have been included in the composite restriction map shown in FIG. 1.

Nucleotide sequencing was initiated for pMON 9418 and 9419. All the DNA sequencing utilized the Sequenase 2.0 kit (International Biotechnologies Inc) using the manufacture's protocol. Although some sequencing used a double stranded template as described above, a single stranded template was preferred. To obtain single stranded DNA template, a colony was inoculated into 2 ml LB broth with 200 μg/ml ampicillin and grown overnight. The culture was then diluted 100 μl into 10 ml 2XYT broth with 200 μg/ml ampicillin and grown to Klett 20 (3-4 hr). Ten μl of M13 helper phage M13KO7 was added and allowed to infect the culture for 1 h before adding 75 μg/ml kanamycin and incubating o/n at 37° C. in shaking water bath. The bacteria were then pelleted and plasmid was purified using the rapid alkaline lysis procedure to confirm by restriction map that the correct recombinant E. coli had been grown. The single stranded DNA was obtained from the phage in the supernatant by filtering the supernatant through a 0.45μ filter and then precipitating the phage with 1.3 ml 15% PEG 8000 in 2.5M NaCl for 5 min on ice. The phage were collected by centrifugation, resuspended in 200 μl TE and lysed by adding 100 μl phenol (saturated in TE) for 5 min at 42° C. The phases were then separated by adding 100 μl 1:1 phenol:chloroform and brief centrifugation. The aqueous phase was re-extracted 1× with 100 μl phenol:chloroform and then 3× with chloroform to further purify the DNA and remove the PEG 8000. The pellet was finally precipitated by adding 1/10 vol 3M sodium acetate and 2 vol 95% ethanol and resuspended in 100 μl TE.

Initial sequencing probes were made using the limited sequence obtained from the T20A/B-T37B PCR product as well as the other two products. Also, degenerate primers were made using other tryptic fragments to obtain some initial sequencing results. As the sequence was obtained, new primers were designed towards the end of the known sequence to continue further through the gene.

After the N-terminal sequence was identified based on its homology to the N-terminal amino acid sequence, it became apparent that the pMON9418 and pMON9419 only contained a partial gene. Therefore, another southern blot experiment was performed using the 14-9 cosmid digested with NcoI+ClaI, NcoI, Not I, SacI, SalI, SphI, XbaI and XhoI. The blot was probed with the NcoI-HindIII fragment. A 3.2 kb SalI fragment was identified and subcloned as described above for the NcoI and HinDIII fragments. The SalI was cloned into Bluescript psK in both orientations giving pMON9421 and pMON9422. These plasmids were then used to obtain the completed restriction map (FIG. 1) and finished sequence (FIG. 2). Referring to FIG. 2, the finished sequence of the PG2982 pehA gene was obtained by completely sequencing both strands of the gene using the standard dG labeling mixture in the Sequenace 2.0 kit and then compressions were resolved by sequencing down the sense strand using the deoxyinosine (dI) labeling mixtures. The sequence has been further confirmed by additional sequencing after each mutagenesis described below. The reading frame was identified based on homology to the tryptic sequences obtained from the purified protein. All the pehA tryptic fragment sequences were found in the deduced pehA amino acid coding sequence. The starting methionine was identified based on its close proximity to the N-terminal tryptic sequence obtained from the purified protein and was the only in-frame methionine between the observed protein N-terminus and an in-frame upstream stop codon. The stop codon was identified as the first in-frame stop codon. The size of the protein encoded by the pehA open reading frame was 58.2 kD which is consistent with the 59 and 66 kD PEH polypeptides observed on SDS-PAGE. The predicted coding sequence was further verified by modifying the gene to include a NcoI at the start site and a SacI at the stop codon inorder to subclone the coding sequence into a Rec A expression vector (the details of this experiment are described below) which produced an active protein assayed using the radioactive in vivo assay and the histochemical XPP assay described above.

MODIFICATION OF THE PG2982 PEHA GENE

In order to fuse the pehA gene to bacterial and plant promoters and to cholorplast transit sequences, the gene was modified to add a NcoI at the starting methionine. To insert the NcoI restriction site, it was also necessary to add in an alanine codon just after the starting methionine.

N-terminal Mutagenesis Primer
GTA AGC CTC GGA AAT AAA GAT CTC ACC ATG GCC AGA AAA AAT GTC CTG (Seq ID No: 16)

Figure 3:
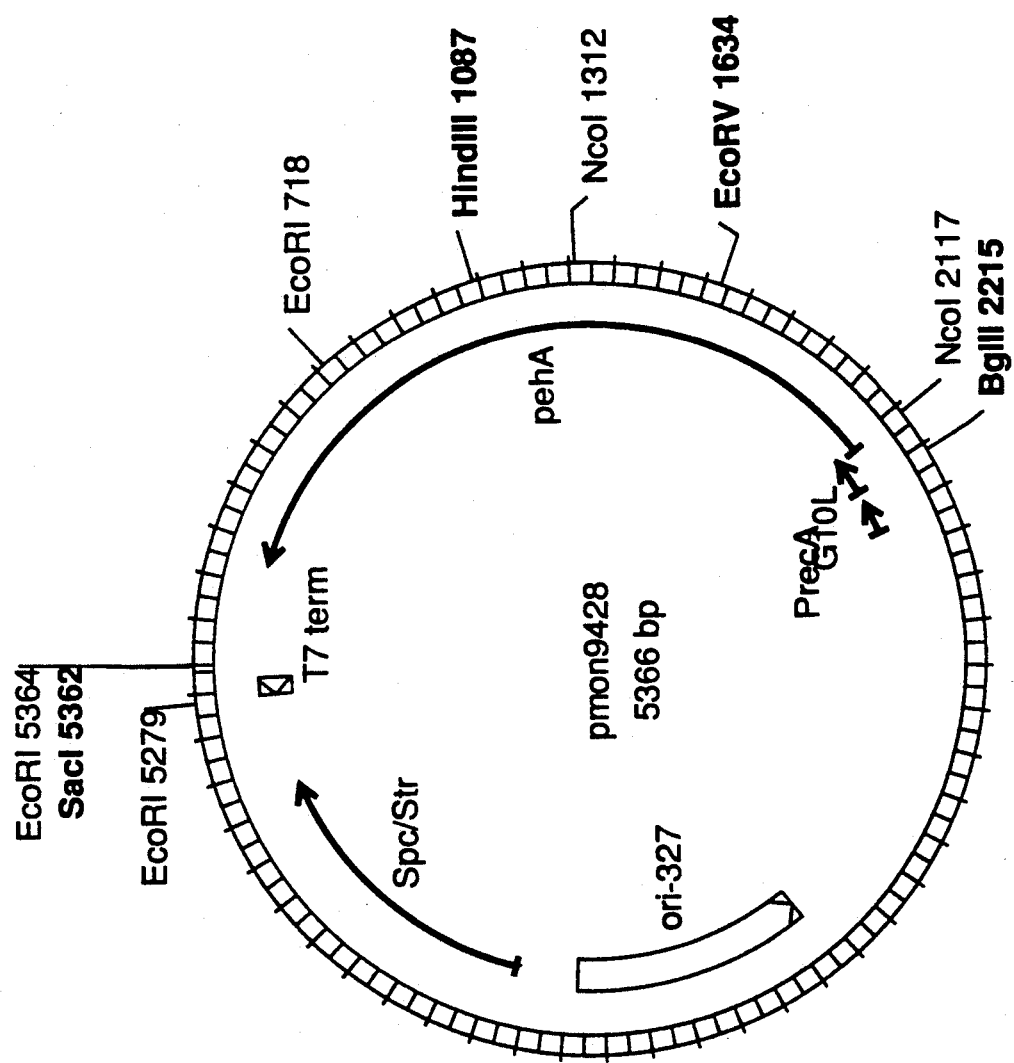
FIG. 3 shows a map of plasmid pMON9428.

The primer used in this experiment as well as other mutagenesis experiments contained the minimal necessary changes flanked by 12 bp on each side of wild-typed sequence. The mutagenesis was carried out on the 14-9 HindIII fragment subcloned into pGem7Zf(+) (Promega) in the orientation to produce the coding strand. Single stranded DNA was purified as described above except that the plasmid was transformed into E. coli strain CJ236 to make a template suitable for mutagenesis. The Kunkel mutagenesis was carried out essentially as described in Maniatis (1982). The primer was phosphorylated by T4 Polynucleotide kinase and then annealed to the template. The mutagenized strand was then synthesized using Klenow polymerase and the ends ligated with T4 ligase. The mutagenesis mixture was then transformed in JM101 and colonies screened for a plasmid which contained the appropriate restriction map if an NcoI was inserted at the start codon. A single isolate was then sequenced to confirm the sequence between the new NcoI site and the BamHI site. The confirmed NcoI to BamHI fragment was then subcloned and ligated with a BamHI to SalI 3' fragment from pMON9422 into pMON5723 yielding pMON 9428 (FIG. 3). The resulting NcoI to SalI pehA gene including some additional 3' non-coding nucleotides was designated pehA:1 or version one of the pehA gene for plant transformation.

To remove the 3' non-coding nucleotides, a SacI site was inserted just after the predicted stop codon. At the same time, primers were designed to remove the internal BamHI, HindIII, NcoI and EcoRI sites. Table VI below lists the primers used to accomplish these modifications.

TABLE VI

| Primer Designed To: | |
| --- | --- |
| Insert SacI | TTG CTC CTG AGC TCA ATG GTT GC (Seq ID No: 17) |
| Remove BamHI | GAA ACG CGG ATC TCT TGC AGA GGT (Seq ID No: 18) |
| Remove HindIII | ATA CGG AAG CTC TCG GCA TTG TA (Seq ID No: 19) |
| Remove NcoI | GAG CCT TCC GCA CCA TGA AAG AAC GAG CC (Seq ID No: 20) |
| Remove EcoRI | CAG ATT GCT GAA CTC ATG CGG GTC (Seq ID No: 21) |

The template for the reaction was the pehA:1 gene subcloned into a Bluescript vector behind the lacz promoter. The pehA gene was active in this vector and yielded blue colonies when XPP was included in the growth medium. Template was made and mutagenized as described above except that the MutaGene kit (BioRad) was used for the mutagenesis steps. The mutagenesis product was transformed into JM101 and plated on XPP plates with IPTG to induce the β-galactosidase promoter. Blue colonies were picked, plasmid prepared using rapid alkaline lysis, and screened for the loss of the 4 internal sites and the presence of the SacI site. A single plasmid was then selected and the complete pehA gene sequence was confirmed by DNA sequencing. The NcoI to SacI pehA gene without common internal restriction sites was designated pehA:2 and the plasmid containing the pehA:2 gene was designated pMON9432.

Further modifications can be made to the pehA:2 gene to improve codon usage for plant gene expression using the above procedures or by the complete chemical synthesis of the pehA coding sequence. Specifically, amino acid codons can be replaced with plant preferred codons for each amino acid. Plant preferred condons have been determined by tabulating codons from many of the plant genes which have been reported in the literature (Murray et al., 1989). Additionally, stretches of purines or pyrimidines greater than 5 bp in length can be broken up by including conservative substitutions for the opposite nucleotide class. Lastly, potential polyadenylation sites can be removed by conservative nucleotide substitutions. These modifications are being contemplated but will be delayed until initial expression data are obtained for pehA:1.

Improvements in the expression of phosphonate monoester hydrolase could also be achieved by expressing the gene using stronger plant promoters, using better 3' polyadenylation signal sequences, optimizing the sequences around the initiation codon for ribosome loading and translation initiation, or by combinations of these or other expression or regulatory sequences or factors.

EXPRESSION, ACTIVITY AND PHENOTYPE OF PHOSPHONATE MONOESTER HYDROLASE IN *ESCHERICHIA COLI*

The phosphonate monoester hydrolase gene was engineered for expression in *E. coli* to confirm the gene was suitable for heterologous expression and resulted in a conditional lethal phenotype. The NcoI-BamHI pehA:1 fragment was removed from pMON9420 by restricting the DNA with both enzymes, separating the fragments on an agarose gel, and purifying the pehA fragment from the gel using the GeneClean kit. In a similar manner the BamHI-ClaI pehA:1 fragment was obtained from pMON9421 and both were ligated into an *E. coli* expression vector to reconstruct the pehA:1 gene behind the RecA promoter with the Lambda gene 10L leader. The resulting vector, pMON9428 (FIG. 3), was transformed into *E. coli* strain JM101 using calcium chloride transformation and transformants selected on LB agar with 100 μg/ml spectinomycin. A single colony was isolated and confirmed by restriction mapping to contain pMON9428. The JM101/pMON9428 was then streaked out on LB agar plates containing 100 μg/ml spectinomycin and 40 ng/ml XPP. As a control, JM101 containing the RecA expression vector without the pehA:1 gene was streaked out on the same plate. The JM101/pMON9428 formed blue colonies while the JM101 with the control vector formed white colonies. This indicated that pehA:1 gene expression can be screened in cells by histochemical staining with XPP and that pehA:1 gene expression, per se, is not lethal. The JM101/pMON9428 and vector control strain were then plated on MOPS minimal medium containing 0.05 mM $HK_2PO_4$ as the phosphate source and 100 μg/ml spectinomycin. Both strains formed colonies as expected since pehA:1 gene expression is not lethal per se. To test for a conditional lethal phenotype, both strains were streaked side by side on a MOPS minimal plate with 0.05 mM $KPO_4$, 100 μg/ml spectinomycin and 10 mM glyceryl glyphosate. The JM101/vector control formed colonies indicating that glyceryl glyphosate was non-toxic to this strain of *E. coli*. However, the JM101/pMON9428 did not form visible colonies indicating that expression of the pehA:1 gene in the presence of a glyphosate ester such as the glyceryl glyphosate resulted in a lethal phenotype. To confirm the lethal phenotype was the result of the degradation of the glyceryl glyphosate and subsequent inhibition of aromatic amino acid biosynthesis by glyphosate, both *E. coli* strains were plated on MOPS minimal medium with 0.05 mM $KPO_4$, 100 μg/ml spectinomycin, 10 mM glyceryl glyphosate and supplemented with aromatic compounds consisting of L-tyrosine, L-tryptophan, L-phenylalanine, each at 100 μg/ml, 2,3-dihydroxybenzoic acid and para-aminobenzoic acid, each at 5 μg/ml. Both the vector control strain and JM101/pMON9428 formed colonies as expected if the aromatic amino acids reversed glyphosate toxicity. This confirmed that the conditional lethal phenotype observed in the presence of the glyceryl glyphosate was the result of its conversion to and subsequent inhibition of EPSPS by glyphosate.

ISOLATION OF A TAPETAL-SPECIFIC PROMOTER

Anther-specific expression can be achieved using a promoter element which specifically regulates the fused coding sequence to express exclusively in an anther. Stamens of tomato (*Lycopersicon esculentum*) were screened for RNA species which were expressed exclusively in the anthers and a promoter for one such RNA was isolated in the present invention. The cDNA clone 127a was demonstrated by differential screening to be a complementary sequence to a tapetal-specific RNA as previously described (Smith et al., 1990). A cDNA library was constructed in a Bluescript (KS+) vector (Stratagene) using polyA RNA isolated from immature anthers of tomato flower buds 8-9 mm in length. The cDNA clone 127a was selected and further characterized by RNA gel blot experiments. Total RNA from pistils and stamens of tomato flowers at anthesis, pistils of flowers with sepal lengths of 8-9 mm, 6-7 mm, 4-5 mm, stamens of flowers with sepal lengths of 8-9 mm, 6-7 mm, 4-5 mm, 14-day-old tomato seedlings, tomato leaves, tomato fruit at the breaker stage of ripening and green tomato fruit was isolated, 20 μg of RNA from each tissue electrophoresed on agarose gels and then blotted to Gene Screen Plus membrane (New England Nuclear). The blot was hybridized with random-oligo-labeled 127a cDNA. The only RNA samples showing hybridization were those of the stamens taken from flower buds with sepal lengths of 8-9 mm, 6-7 mm, and 4-5 mm. Stamens expressing 127a RNA were shown to contain pollen at a developmental stage from early meiosis until the dissolution of tetrads. The Bluescript (KS+) plasmid containing the cDNA 127a was designated pMON8808.

The expression of gene 127a was further determined to be limited to the tapetal cell layer of the stamens by in situ hybridization. Strand specific radioactive RNA probes for 127a were produced from pMON8808 using the T3 and T7 polymerase promoters on the Bluescript (KS+) vector. These strand specific probes were hybridized with 10 μm sections of tomato flowers having sepals 4-10 mm in length using the method of (Smith et al., 1987). The flower sections were exposed to a photographic emulsion to visualize the localization of hybridized probe. These experiments demonstrated the expression of the 127a gene was only detectable in the tapetal tissue of tomato stamens (Smith et al., 1990).

Figure 4:
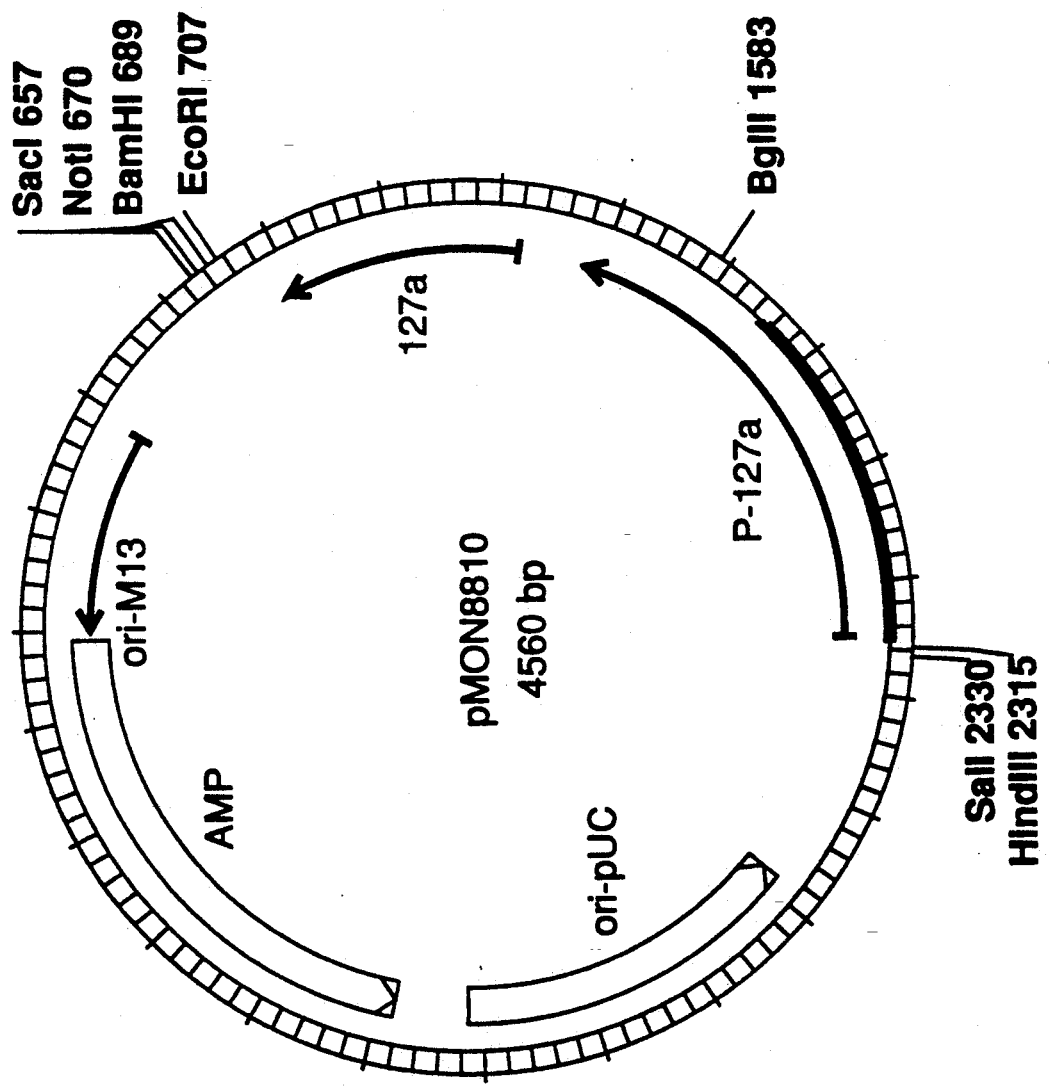
FIG. 4 shows a map of plasmid pMON8810.

The promoter conferring temporal and spatial tapetal-specific expression of 127a was then isolated. A tomato genomic library (Budelier et al., 1990) was screened with the radiolabeled cDNA insert from pMON8808. A lambda clone designated 45c was isolated that when digested with the restriction endonuclease Cla I released a 3.0 kb fragment that hybridized strongly to the 127a cDNA clone. This 3.0 kb fragment was subcloned into the plasmid vector Bluescript (KS+) forming pMON8809. The homology between the 127a cDNA clone and pMON8809 was further localized to a 1.6 kb ClaI to EcoRI restriction fragment. This 1.6 kb fragment was subcloned from pMON8809 as a HindIII to EcoRI fragment into similarly digested Bluescript (KS+) plasmid to form pMON8810 (FIG. 4). The orientation of the transcript from the 127a gene was determined by hybridizing radio-labeled strand specific probes with RNA gel blots. The complete sequence of the 127a cDNA was determined using pMON8808 and combined with additional sequence of the genomic clone in pMON8810 using Sanger dideoxy sequencing (FIG. 5) (Sanger et al., 1977). The co-alignment of the sequences indicated that there were no introns contained in the 127a gene.

The start of transcription of the 127a gene was determined by primer extension using the methods described by (Budelier et al., 1990). An oligonucleotide with the sequence 5'-AATCGTGGTT GCCATGGTGCCTAGG-3' (Seq ID No: 22)

that was homologous to the sequences 471 to 487 of pMON8810 (numbering 3'-5' from the EcoRI site) but containing an NcoI site not found in pMON8810 was used to prime the synthesis of first strand cDNA from polyA(+) RNA. A major 142 bp product was produced indicating the start of transcription to be at nucleotide 345 of pMON8810 and corresponded exactly with the 5' end of the cDNA in pMON8808.

Figure 6:
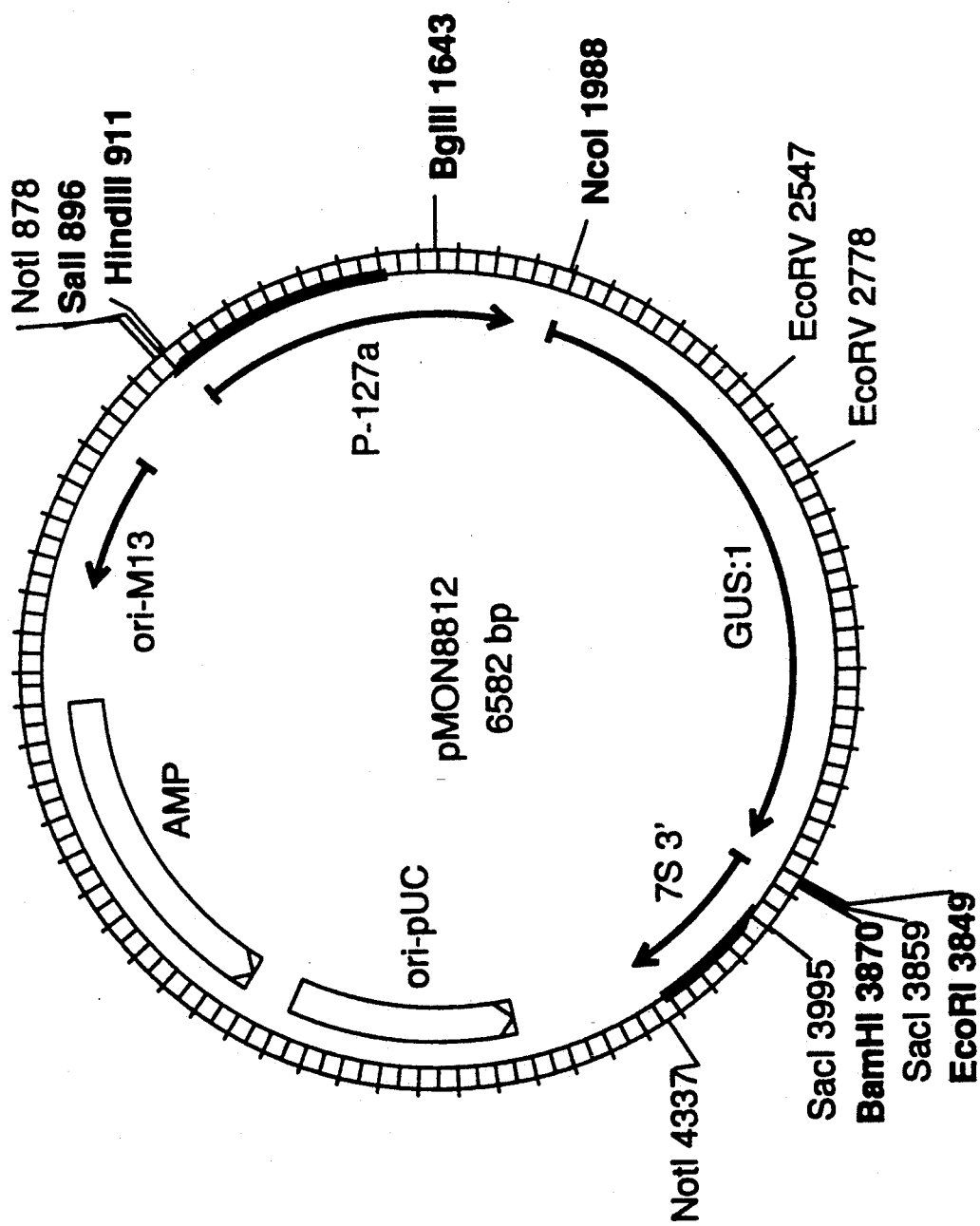
FIG. 6 shows a map of plasmid pMON8812.

In order to subclone the tapetal-specific promoter fragment from the 127a genomic clone, a NcoI restriction site was introduced at the translation start codon. The site was introduced into pMON8810 with the oligonucleotide used previously for primer extension (Seq ID No: 22). Single stranded DNA corresponding to the sense strand of pMON8810 was rescued according the methods outlined by Stratagene in the host *E. coli* BW313. The mutagenesis primer was annealed, extended, and transformed into *E. coli* JM101 (Budelier et al., 1990). The resulting colonies where screened for the introduced NcoI site by restriction endonuclease digestion with NcoI. The mutagenized plasmid was designated pMON8811. The tapetal-specific promoter was removed from pMON8811 on an approximately 1,000 bp SalI to NcoI fragment by digesting the plasmid with NcoI and SalI. The 5,487 bp fragment from an NcoI and SalI restriction endonuclease digestion of pMON637 was ligated with the 1,000 bp SalI to NcoI fragment of pMON8811 to generate pMON8812. This construction placed the tapetal-specific promoter in an orientation to drive the expression of β-glucuronidase with the polyadenylation signal from the 7S seed storage protein gene of soybean (FIG. 6).

Figure 7:
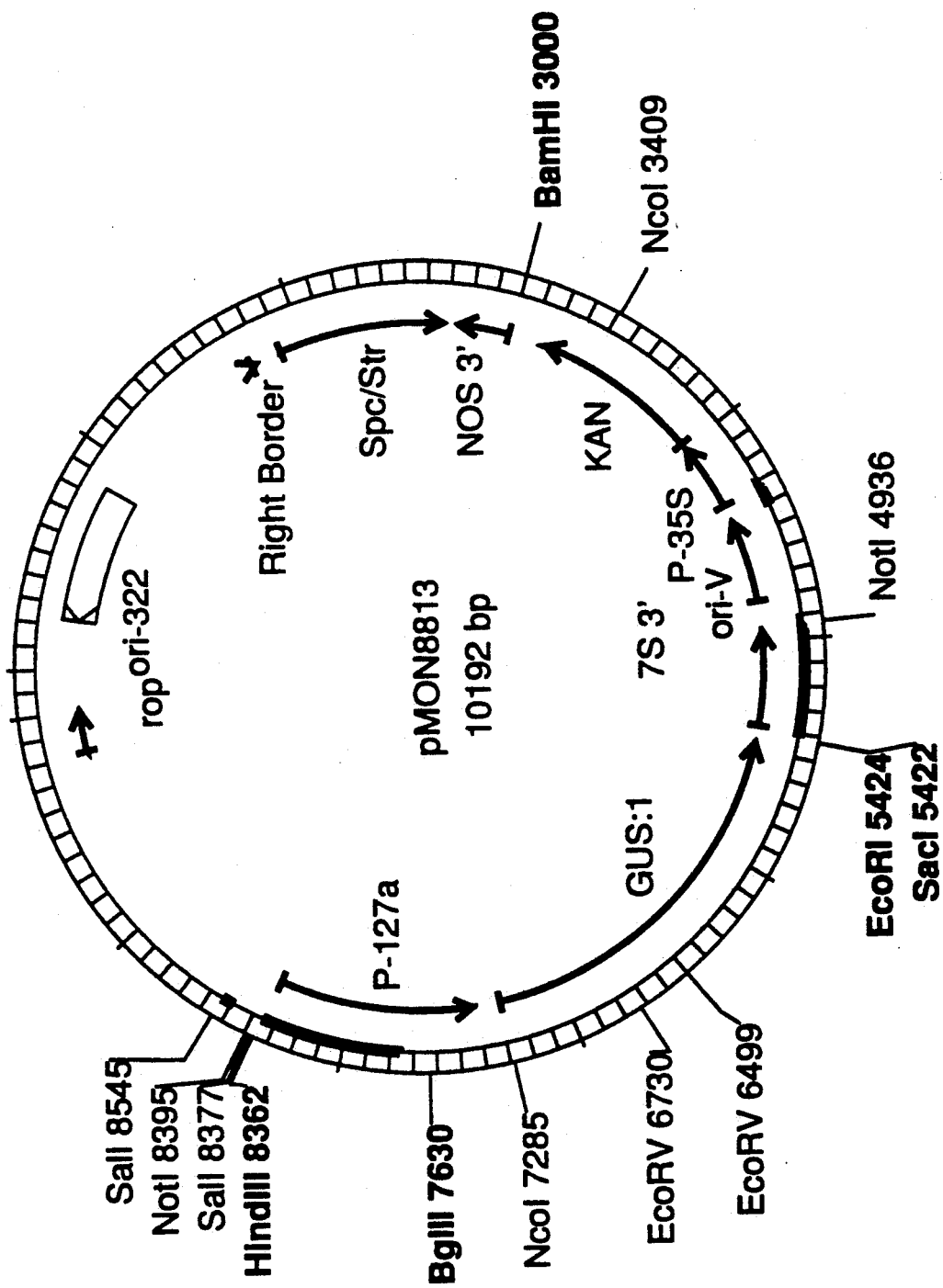
FIG. 7 shows a map of plasmid pMON8813.

The p127a promoter fused to GUS was transformed into model plant systems to demonstrate that the promoter was capable of expressing a heterologous sequence in a spatial and temperal specific manner within the tapetum. The vector, pMON8812, was digested with Not I to release a fragment of approximate 3,400 bp in length containing the p127a promoter with the GUS coding sequence and the 7S 3' sequence. This Not I fragment was ligated to the *Agrobacterium tumefaciens* transformation vector pMON886 that had been digested with Not I. The resulting plasmid, designated pMON8813 (FIG. 7) was mated into *Agrobacterium tumefaciens* strain ACO by a tri-parental procedure with a second *E. coli* containing the plasmid PRK2013 (Fraley et al., 1985). The resulting *Agrobacterium tumefaciens* strain ACO carrying a co-integrated pMON8813 into the Ti plasmid was designated 17D.

*Lycopersicon esculentum* cv. UC82B and *Nicotiana tabacum* cv. Samsun were transformed with 17D according to the methods of McCormick et al., 1986; Horsch et al., 1985, respectively. Regenerated plants (R0) were analyzed for expression of β-glucuronidase in all tissues of the plant. Hand sections were produced and analyzed for β-glucuronidase activity using the histochemical substrate 5-bromo-4-chloro-3-indolyl-β-D-glucuronide (X-gluc) (Jefferson et al., 1987). When tissue sections were incubated in an X-gluc concentration of 10 mg/ml at 25° C. for one hour β-glucuronidase activity was only detectable in the tapetal tissue of stamens from buds 4-9 mm in length. This corresponded exactly with the timing of expression of the endogenous 127a gene. If hand sections of young petioles and roots from R0 plants where incubated in an X-gluc concentration of 50 mg/ml at 37° C. for four hours, slight β-glucuronidase activity could be detected in the regions of the vascular traces of these organs. No other β-glucuronidase activity was detected in the transgenic tomato or tobacco plants. Selfing these plants produced the R1 generation of plants that showed normal Mendelian inheritance of the tapetal-specific β-glucuronidase activity with no change in expression pattern.

PLANT TRANSFORMATION

Plants which can be transformed to express the phosphonate monoester hydrolase gene in the practice of the present invention include, but are not limited to, soybean, cotton, corn, canola, oil seed rape, flax, sugarbeet, sunflower, potato, tobacco, tomato, wheat, rice, alfalfa and lettuce.

A double-stranded DNA molecule of the present invention ("chimeric phosphonate monoester hydrolase gene") can be inserted into the genome of a plant by any suitable method. Suitable plant transformation vectors include those derived from a Ti plasmid of *Agrobacterium tumefaciens*, as well as those disclosed, e.g., by Herrera-Estrella (1983), Bevan (1984), Klee (1985) and EPO publication 120,516 (Schilperoort et al.). In addition to plant transformation vectors derived from the Ti or root-inducing (Ri) plasmids of agrobacterium, alternative methods can be used to insert the DNA constructs of this invention into plants cells. Such methods may involve, for example, the use of liposomes, electroporation, chemicals that increase free DNA uptake, free DNA delivery via microprojectile bombardment, and transformation using viruses or pollen.

PLANT TRANSFORMATION VECTORS pMON886 is made up of the following segments of DNA. The first is a 0.93 kb AvaI to engineered-EcoRV fragment isolated from transposon Tn7 that encodes bacterial spectinomycin/streptomycin resistance (Spc/Str), which is a determinant for selection in *E. coli* and *Agrobacterium tumefaciens*. This is joined to the 1.61 kb segment of DNA encoding a chimeric kanamycin resistance which permits selection of transformed plant cells. The chimeric gene (P-35S/KAN/NOS 3') consists of the cauliflower mosaic virus (CaMV) 35S promoter (Odell et al., 1985), the neomycin phosphotransferase type II (KAN) gene, and the 3'-nontranslated region of the nopaline synthase gene (NOS 3') (Fraley et al., 1983). The next segment is the 0.75 kb oriV containing the origin of replication from the RK2 plasmid. It is joined to the 3.1 kb SalI to PvuI segment of pBR322 (ori322) which provides the origin of replication for maintenance in *E. coli* and the bom site for the conjugational transfer into the *Agrobacterium tumefaciens* cells. The next segment is the 0.36 kb PvuI to BclI from pTiT37.

The pMON10098 plant transformation vector incorporates most of the same vector segments as pMON886 except their arrangement in the plasmid has been changed and furthermore includes the right and left T-DNA borders flanking the genes of interest and the selectable marker gene. The order of the DNA segments begins with a 0.36 Kb PvuI to BclI fragment from the pTiT37 plasmid which contains the nopaline-type T-DNA right border region. The next segment contains the enhanced CaMV35S promoter (Kay et al., 1987) in front of a poly-cloning site where a gene of interest can be inserted followed by the pea ribulose-1,5-bis-phosphate carboxylase small subunit E9 3' non-translated region (Coruzzi et al., 1984 and Morelli et al., 1985). The next segment contains some additional unique restriction sites to insert a second gene of interest. The next segment is the chimeric kanamycin resistance gene (CaMV35S/NPTII/NOS 3') engineered as a plant selectable marker. This is joined to the 0.45 Kb ClaI to DraI fragment from the pTi15955 octapine Ti plasmid which contains the T-DNA left border region (Barker et al., 1983). Next is the 0.75 Kb oriV segment containing the origin of replication from the RK2 plasmid. This is joined to the 3.0 Kb SalI to PstI segment of pBR322 which provides the origin of replication for maintenance in *E. coli* (ori-322). The last fragment is the 0.93 Kb piece of DNA isolated from transposon Tn7 which encodes bacterial Spc/Str resistance.

The plant vectors were mobilized into the ABI Agrobacterium strain. The ABI strain is the A208 *Agrobacterium tumefaciens* carrying the disarmed Ti plasmid pTiC58 (pMP90RK) (Koncz and Schell, 1986). The Ti plasmid does not carry the T-DNA phytohormone genes and the strain is therefore unable to cause the crown gall disease. Mating of the plant vector into ABI was done by the triparental conjugation system using the helper plasmid pRK2013 (Ditta et al., 1980). When the plant tissue is incubated with the ABI::plant vector conjugate, the vector is transferred to the plant cells by the vir functions encoded by the disarmed pTiC58 plasmid. The vector opens at the T-DNA right border region, and the entire plant vector sequence may be inserted into the host plant chromosome. The pTiC58 Ti plasmid does not transfer to the plant cells but remains in the Agrobacterium.

PLANT REGENERATION

After transformation of cells (or protoplasts), choice of methodology for the regeneration step is not critical, with suitable protocols being available for hosts from Leguminosae (alfalfa, soybean, clover, etc.). Umbelliferae (carrot, celery, parsnip), Cruciferae (cabbage, radish, rapeseed, etc.), Cucurbitaceae (melons and cucumber), Gramineae (wheat, rice, corn, etc.), Solanaceae (potato, tobacco, tomato, peppers) and various floral crops (see, e.g., Ammirato, 1984; Shimamoto, 1989; Fromm, 1990; Vasil, 1990).

EXAMPLES

The transformation, expression and activity of phosphonate ester hydrolase and the conditional lethal phenotype imparted to cells by the expression of the phosphonate monoester hydrolase in the presence of glyphosate phosphonate esters is described in the following exemplary embodiments.

The following examples are provided to better elucidate the practice of the present invention and should not be interpreted in any way to limit the scope of the present invention. Those skilled in the art will recognize that various modifications, truncations, etc. can be made to the methods and genes described herein while not departing from the spirit and scope of the present invention.

EXAMPLE 1

Figure 8:
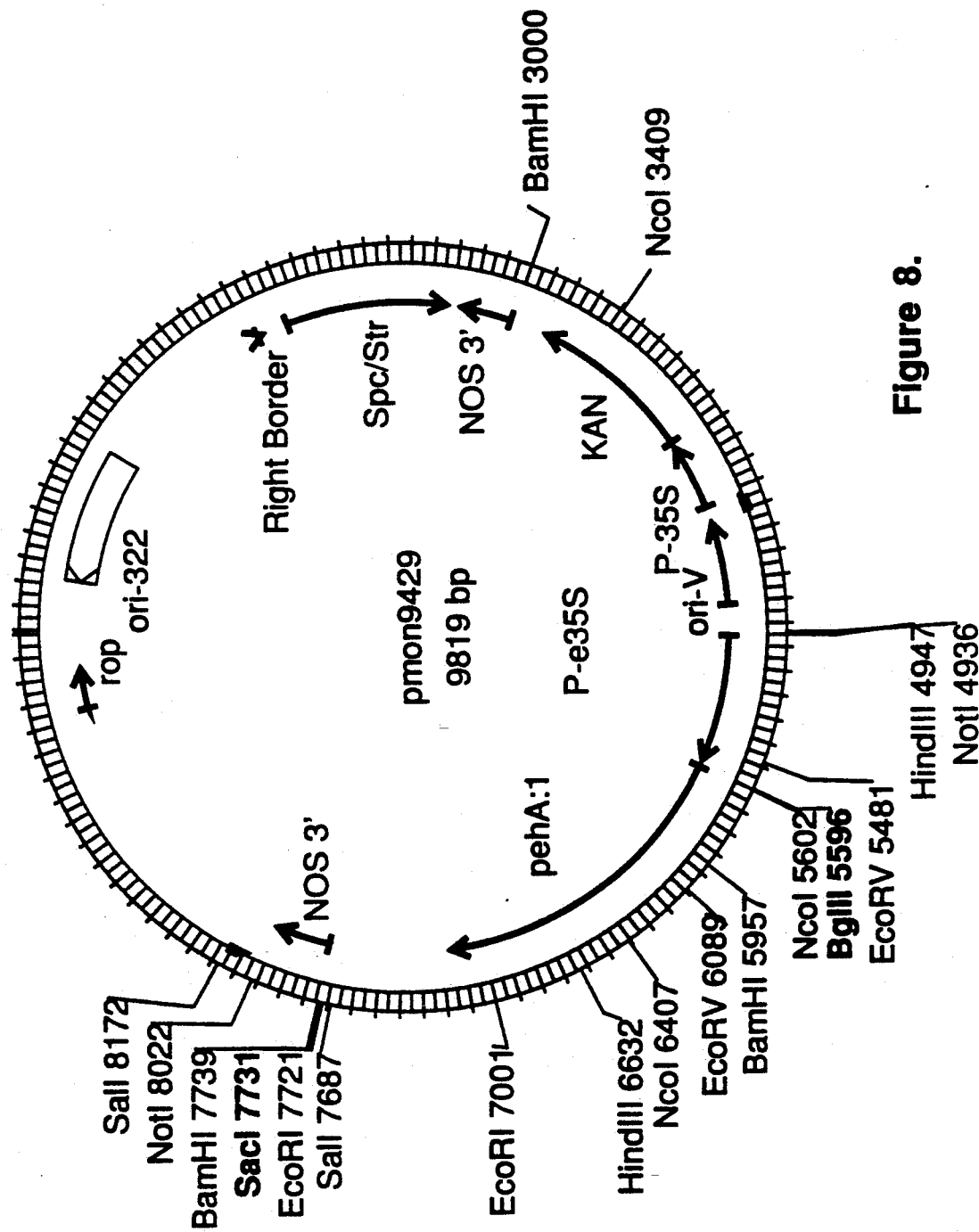
FIG. 8 shows a map of plasmid pMON9429.
Figure 9:
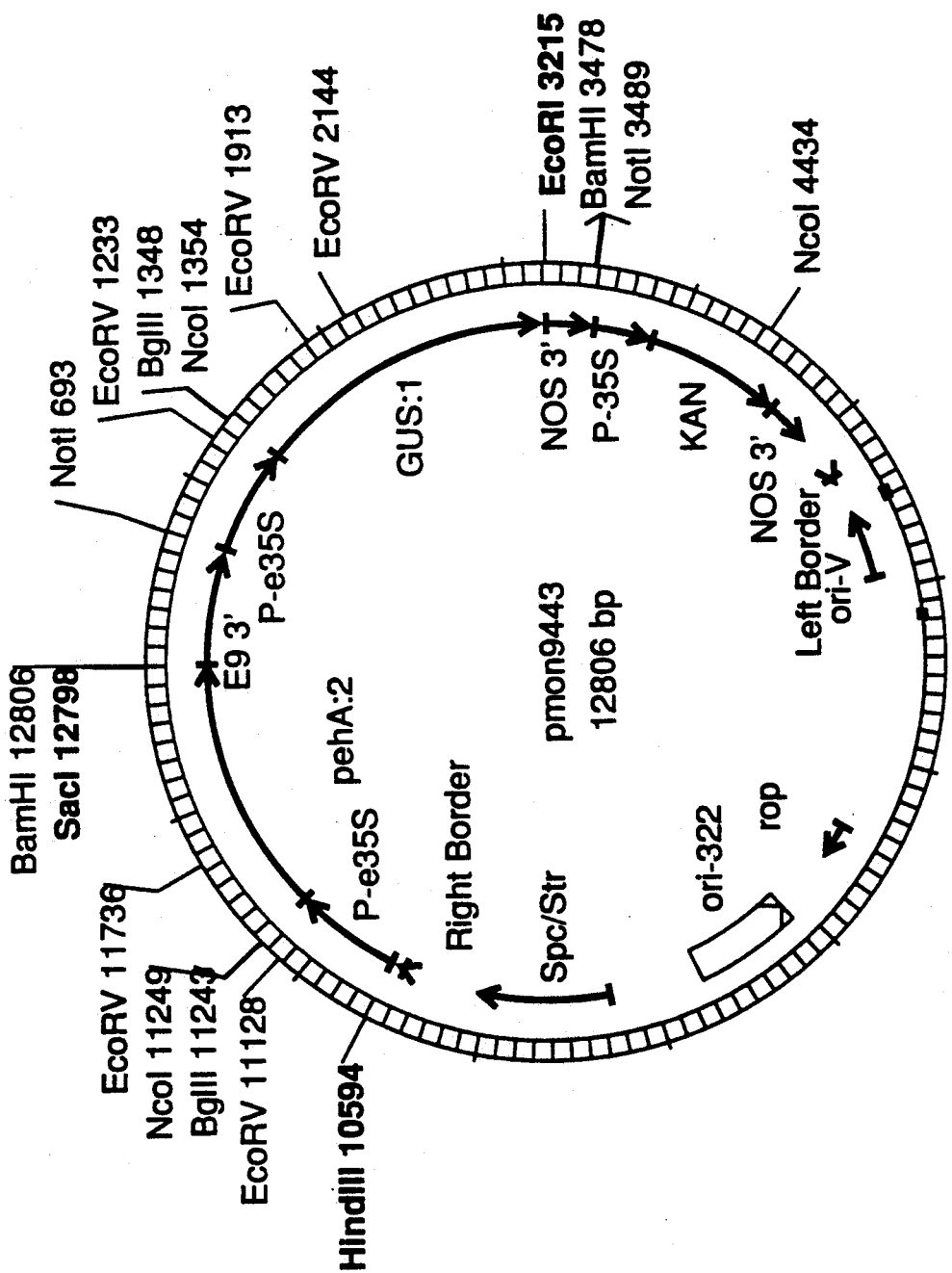
FIG. 9 shows a map of plasmid pMON9443.

Expression, Activity and Phenotype of Phosphonate Monoester Hydrolase in Arabidopsis The phosphonate monoester hydrolase was engineered for constitutive expression in plants to confirm the gene was suitable for plant expression and resulted in a conditional lethal phenotype. The pehA:1 gene was first ligated to the cauliflower mosaic virus enhanced CaMV35S promoter (Kay et al., 1987). The plasmid pMON9428 was digested with NcoI and BamHI and in a separate reaction, BamHI and SacI. The fragments were separated on an agarose gel and the pehA:1 N-terminal NcoI-BamHI fragment and the C-terminal BamHI-SacI fragment purified using the GeneClean kit. The pehA:1 gene was then reconstructed by ligation into pMON999 previously digested with NcoI and SacI. The resulting plasmid was designated pMON9426 and contained the pehA:1 gene behind the enhanced CaMV35S promotor with the Nos polyA signal on a NotI fragment. The NotI fragment was then excised from pMON9426 and inserted at the NotI site of the plant transformation vector, pMON886, resulting in the vector pMON9429 (FIG. 8). The pehA:2 gene was similarly engineered for constitutive plant expression. The pehA:2 gene, contained within a BlgII to SaeI restriction fragment, was ligated behind the enhanced CaMV35S promoter in the plant transformation vector pMON10098 to give pMON9438. The pMON9438 plasmid was then digested with NotI and a NotI restriction fragment containing the enhanced CaMV35S promoter fused to the β-glucuronidase (GUS) gene with the NOS 3', was inserted to give pMON9443 (FIG. 9). The pMON9429 and pMON9443 vectors were then mobilized into an ABI Agrobacterium strain for Arabidopsis transformation.

Arabidopsis Transformation Protocol

Arabidopsis was cultured and transformed essentially as described by Valvekens et al., 1988. Arabidopsis ecotype RLD seeds were sterilized in 5% chlorox, 0.05%. Tween20 for 20 min, washed with sterile $H_2O$ and plated on MSO medium (MS salts with minimal organics (Sigma), 0.5 g MES/l pH 5.7, 1% sucrose and 0.8% agar). After 3 weeks the roots were cut away from the shoots and precultured 3 days on callus inducing medium (CIM; Gamborg's B5 salts (Sigma), 2% glucose, 0.5 g/l MES, pH 5.7, 0.8% agar, 0.5 mg/l 2,4-D and 0.05 mg/l kinetin). The roots were than grouped in small bundles of 5-7 roots and cut into 0.5 cm pieces. The root pieces were mixed with a fresh overnight culture of ABI Agrobacterium containing a previously described plant gene expression vector diluted 1:20 in liquid MSO (without agar). After two minutes, the roots were transferred to fresh CIM plates for a two day co-culture. After co-culture, the root pieces were washed 2X with liquid MSO medium and plated on shoot inducing medium (SIM; Gamborg's B5 salts, 2% glucose, 0.5 g/l MES, pH 5.7, 5 mg/l $N^6$-(2-isopentenyl)adenine, 0.15 mg/l indole-3-acetic acid, 500 mg/l carbenicillin, 100 mg/l kanamycin and 0.8% agar. Callus which continued to grow and remain green were transformed to fresh SIM after two weeks. As rosettes began to form, they were cut away from the callus and transferred to MSO medium with 1 mg/l indole-3-butyric acid in sterile sundae cups to initiate root formation. After the plants had formed roots they were transferred to soil and grown to maturity to obtain seed.

Phosphonate Monoester Hydrolase Expression Results

Arabidopsis calli transformed with either pMON9429 or pMON9443 which were expressing the selectable marker NPT-II gene as evidenced by growth on 100 μg/ml kanamycin were then evaluated for pehA expression. The calli were transferred to SIM medium containing 100 μg/ml kanamycin and 1 mM glyceryl glyphosate. After 4 weeks, calli were scored for growth and ability to initiate shoots and leaves (+) or for necrosis (−). Table VII below shows the results of this experiment.

TABLE VII

| Independent Callus Genotype | Lines Scored | Viability Score | |
|---|---|---|---|
| | | Growth | Necrosis |
| | | number of lines | |
| pMON9429 Transgenic | 6 | 1 | 5 |
| mMON9443 Transgenic | 6 | 0 | 6 |
| GUS Vector Control | 12 | 12 | 0 |

The observation that the control calli were able to grow on 1 mM protoxin (glyceryl glyphosate) provides additional evidence that the phosphonate esters of glyphosate are not toxic per se. The observed lethality of pMON9429 and pMON9443 calli when plated on medium containing the glyceryl glyphosate confirms the hypothesis that the pehA:1 and pehA:2 genes can be expressed in plant cells and that expression in the presence of a phosphonate ester of glyphosate has a lethal phenotype. The lethal phenotype was not the result of the pehA genes per se since the calli were able to grow on medium without the glyceryl glyphosate but resulted from the PEH enzymatic hydrolysis of a phosphonate ester of glyphosate and subsequent inhibition of aromatic amino acid biosynthesis. The observed conditional lethal phenotype substantiates the use of the pehA:1 and pehA:2 genes as negative selectable markers.

EXAMPLE 2

Anther-Specific Expression of the pehA gene in Arabidopsis

Figure 10:
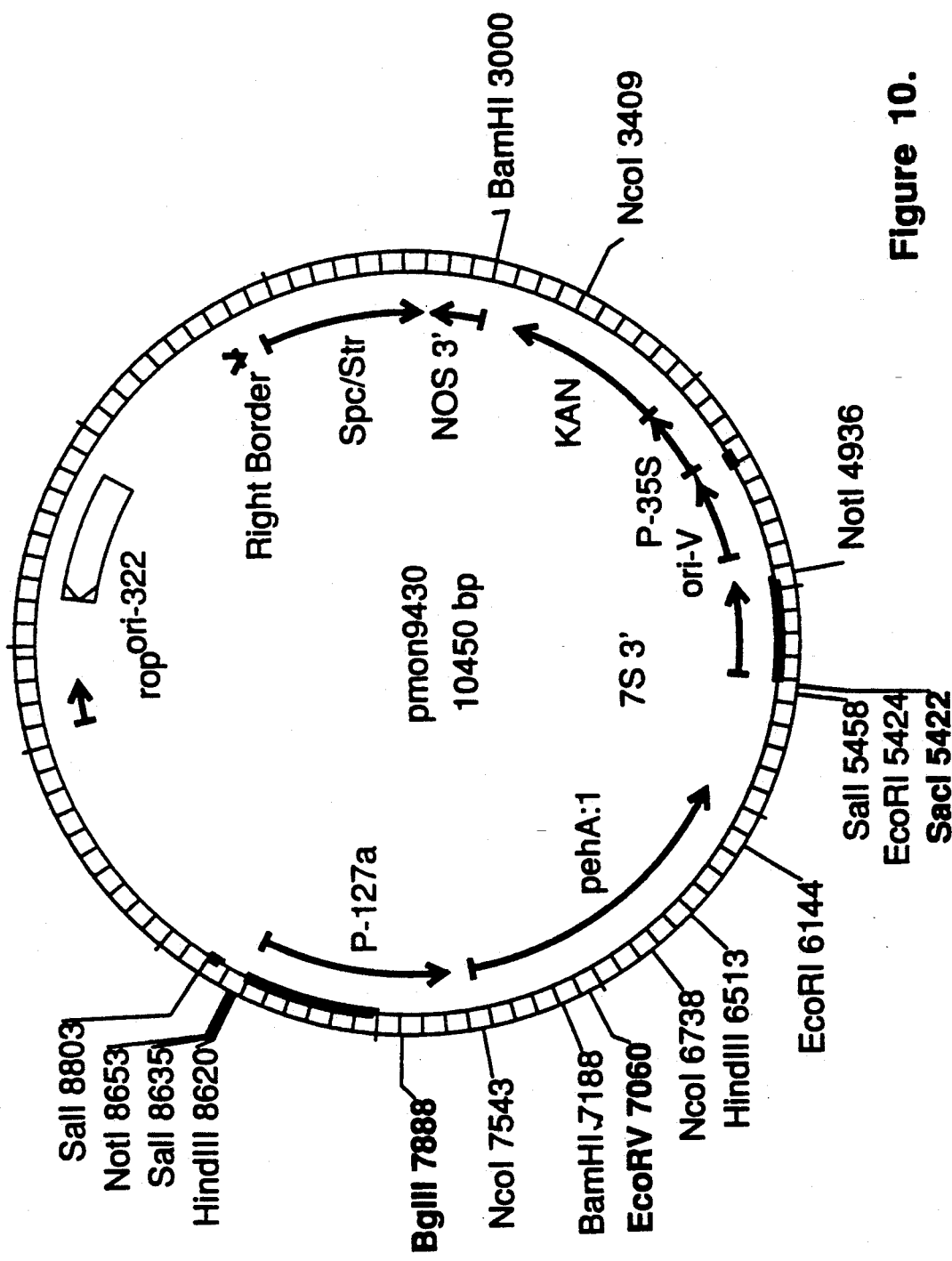
FIG. 10 shows a map of plasmid pMON9430.

The pehA:1 gene was engineered for anther-specific expression to demonstrate cell ablation and specifically, conditional (inducible) male sterility. The pehA:1 gene was excised intact from pMON9428 after partial digestion with both NcoI and EcoRI. The NcoI to EcoRI was then ligated into pMON8812 behind the p127a tapetal specific promoter with the 7S polyadenylation signal and the resulting vector designated pMON9427. The NotI fragment containing the p127a-pehA-7S construct was moved into the NotI site of pMON886 giving the vector, pMON9430 (FIG. 10). The pMON9430 vector was then mobilized into ABI Agrobacterium and used for Arabidopsis tranformation as described above.

At the time the Ro plants initiated flowers, several umbels were removed from each plant and pehA gene activity was assayed using the histochemical stain. After 4-24 hours in the XPP histochemical stain, blue staining of anthers from transgenic Arabidopsis was observed in 9 out of 10 of the first plants to flower while control anthers remained colorless. The blue staining appeared in only young anthers which were well-formed but prior to anthesis. Transgenic anthers in the very youngest flowers and flowers which were past anthesis remained colorless indicating that the developmental timing of the p127a promoter was similar to tomato and tobacco. These observations indicate the pehA:1 gene can be expressed in a tissue specific manner necessary for cell ablation. Specifically, these results indicate the pehA:1 gene can be expressed in an anther-specific manner to allow for conditional male sterility.

From the foregoing, it will be seen that this invention is one well adapted to attain all the ends and objects hereinabove set forth together with advantages which are obvious and which are inherent to the invention. It will be understood that certain features and subcombinations are of utility and may be employed without reference to other features and subcombinations. This is contemplated by and is within the scope of the claims. Since many possible embodiments may be made of the invention without departing from the scope thereof, it is to be understood that all matter herein set forth or shown in the accompanying figures is to be interpreted as illustrative and not in a limiting sense.

BIBLIOGRAPHY

Ammirato, P. V. et al. (1984) *Handbook of Plant Cell Culture-Crop Species.* Macmillan Publ. Co.

Barker, R. F., K. B. Idler, D. V. Thompson and J. D. Kemp. (1983) Nucleotide sequence of the T-DNA region from the *Agrobacterium tumefaciens* ocatopine Ti plasmid pTi15955. Plant Mol. Biol. 2:335–350.

Bevan, M., (1984) Nucl. Acids Res. 12:8711–8721.

Budelier K. A., A. G. Smith and C. S. Gasser (1990) Regulation of a stylar transmitting tissue-specific gene in wild-type and transgenic tomato and tobacco. Mol. Gen. Genetics. (in press).

Birnboim, H. C. and J. Doly (1979) A rapid alkaline extraction procedure for screening recombinant plasmid DNA. Nucl. Acids Res. 7:1513–1525.

Brown, S. M. and M. L. Crouch (1990) Characterization of a gene family abundantly expressed in *Oenothera organensis* pollen that shows sequence similarity to polygalacturonase. Plant Cell 2:263–274.

Coruzzi, G., R. Broglie, C. Edwards and N. H. Chua. (1984) Tissue-specific and light-regulated expression of a pea nuclear gene encoding the small subunit of ribulose-1,5-bisphosphate carboxylase. EMBO 3:1671–1679.

Cowell, J. E., J. L. Kunstman, P. J. Nord, J. R. Steinmetz and G. R. Wilson (1968) Validation of an analytical residue method for analysis of glyphosate and metabolite: An interlaboratory study. J. Agric. Food Chem. 34:955–960.

Davis, B. J. (1964) Ann. N.Y. Acad. Sci. 121:404.

Devereux, J., P. Haeberli and O. Smithies (1984) A comprehensive set of sequence analysis programs for the VAX. Nucl. Acids Res. 12:387–395.

Ditta, G., S. Stanfield, D. Corbin and D. R. Helinski (1980) Broad host range DNA cloning system for Gram-Negative bacteria: construction of a gene bank of *Rhizobium meliloti*. Proc. Natl. Acad. Sci. USA 77,7347–7351.

Elion, G. B. (1978) J. Biol. Chem. 253:8721–8727.

Fabijanski, S. F. (1990) Application of Anti-sense RNA for the regulation of fertility in plants. Developments in antisense technology for commercial applications in human therapy and agriculture. In Developments in anti-sense technology for commercial applications in human therapy and agriculture. Meeting abstract.

Fehr, W. (1987) *Principles of Cultivar Development.* Macmillan Publ. Co., New York, N.Y.

Fraley, R. T., S. G. Rogers, R. B. Horsch, P. R. Sanders, J. S. Flick, S. P. Adams, M. L. Bittner, L. A. Brand, C. L. Fink, J. S. Fry, G. R. Galluppi, S. B. Goldberg, N. L. Hoffmann and S. C. Woo (1983) Expression of bacterial genes in plant cells. Proc. Natl. Acad. Sci. USA 80:4803–4807.

Fraley, R. T., S. G. Rogers, R. B. Horsch, D. A. Eichholtz, J. S. Flick, C. L. Fink, N. L. Hoffmann and P. R. Sanders (1985) The SEV system: a new disarmed Ti plasmid vector system for plant transformation.

Fromm, M. (1990) UCLA Symposium on Molecular Strategies for Crop Improvement, Apr. 16–22, 1990. Keystone, Colo.

Hallas, L. E., E. M. Hahn and C. Korndorfer (1988) Characterization of microbial traits associated with glyphosate biodegradation in industrial activated sludge. J. Industrial Microbiol. 3:377–385.

Hames, B. D. (1985) An introduction to polyacrylamide gel electrophoresis. in B. D. Hames and D. Rickwood (ed). Gel Electrophoresis of proteins. IRL Press, Oxford. pp. 1–86.

Hanson, D. D., D. A. Hamilton, J. L. Travis, D. M. Bashe and J. P. Mascarenhas (1989) Characterization of a pollen-specific cDNA clone from *Zea mays* and its expression. Plant Cell 1:173–179.

Heitkamp, M. A., L. Hallas and W. J. Adams (1990) Biotreatment of industrial wastewater with immobilized microorganisms. Presented in Session 11, Paper S40, Society for Industrial Microbiology Annual Meeting, Orlando, Fla., Jul. 29–Aug. 3, 1990.

Herrera-Estrella, L. et al. (1983) Nature 303:209.

Hohn, B. and J. Collins (1980) A small cosmid for efficient cloning of large DNA fragments. Gene 11:291–298.

Horsch, R. B., J. Fry, N. L. Hoffmann, M. Wallroth, D. Eichholtz, S. G. Rogers and R. T. Fraley. (1985) A simple and general method for transferring genes into plants. Science 227:1229–1231.

Jefferson, R. A., T. A. Kavanaugh and M. W. Bevan (1987) EMBO J., 6:3901–3907.

Kay, R., A. Chan, M. Daly and J. McPherson (1987) Duplication of the CaMV35S promoter sequences creates a strong enhancer for plant genes. Science 236:1299–1302.

Kelly, S. J. and L. G. Butler (1975) Enzymatic hydrolysis of phosphonate esters. Bioch. Biophys. Res. Comm. 66:316–321.

Klee, H. J. et al. (1987) Genes Dev. 1:86–96.

Klee, H. J. et al. (1985) Bio/Technology 3:637–42.

Koncz, C. and J. Schell (1986) The promoter of T$_L$-DNA gene 5 controls the tissue-specific expression of chimeric genes carried by a novel type of Agrobacterium binary vector. Mol. Gen. Genet. 204:383–396.

Kunkel, T. A., J. D. Roberts and R. A. Zakour (1987) Rapid and efficient site-specific mutagenesis without phenotypic selection. Methods Enzymol. 154:367.

Landel, C. P., J. Zhao, D. Bok and G. A. Evans (1988) Lens-specific expression of recombinant ricin induces developmental defects in the eyes of transgenic mice. Genes Develop. 2:1168–1178.

Lasar, K. D. and N. R. Larsten (1972) Anatomy and Cytology of microsporogenesis in cytoplasmic male sterile angiosperms. Bot. Rev. 38:425–454.

Lee, S.-L. J. and H. E. Warmke (1979) Organelle size and number in fertile and T-cytoplasmic male-sterile corn. Amer. J. Bot. 66:141–148.

Malik, J., G. Barry and G. Kishore (1989) The herbicide glyphosate. Biofactors 2:17–25.

Maniatis, T., E. F. Fritsch and J. Sambrook (1982) Molecular Cloning: a laboratory manual. Cold Spring Harbor Laboratory, Cold Spring Harbor, N.Y.

Mansour, S. L., K. R. Thomas and M. R. Capecchi (1988) Disruption of the proto-oncogene int-2 in mouse embryo-derived stem cells: a general strategy for targeting mutations to non-selectable genes. Nature 336:348–352.

Mariani, C., M. DeBeuckeleer, J. Truettner, J. Leemans and R. Goldberg (1990) Induction of male sterility in plants by a chimaeric ribonuclease gene. Nature 347:737–741.

McCromick, S., J. Niedermeyer, A. Barnson, R. Horsch, R. Fraley (1986) Leaf disc transformation of cultivated tomato (L. Esculentum) using *Agrobacterium tumefaciens*. Plant Cell Reports 5:81–84.

Miller, J. H. (1972) Experiments in Molecular Genetics. Cold Spring Harbor Laboratory, Cold Spring Harbor, N.Y.

Moore, J. K., H. D. Braymer and A. D. Larson (1983) Isolation of a Pseudomonas sp. which utilizes the phosphonate herbicide glyphosate. Appl. Environ. Microbiol. 46:316–320.

Morelli, G., F. Nagy, R. T. Fraley, S. G. Rogers and N. H. Chua (1985) A short conserved sequence is involved in the light-inducibility of a gene encoding ribulose 1,5-bisphosphate carboxylase small subunit of pea. Nature 315:200–204.

Mueller, A. J. and R. Grafe (1978) Isolation and characterization of cell lines of *Nicotiana tobacum* lacking nitrate reductase. Mol. Gen. Genet. 182:301–304.

Murray, E. E., J. Lotzer and M. Eberle (1989) Codon Usage in plants. Nucl. Acids Res. 17:477–498.

Odell, J. T., F. Nagy, and N. H. Chua (1985) Identification of DNA sequences required for activity of the cauliflower mosaic virus 35S promoter. Nature 313, 810–812.

Palmiter, R. D., R. R. Behringer, C. J. Quaife, F. Maxwell, I. H. Maxwell and R. L. Brinster (1987) Cell lineage ablation in transgenic mice by cell-specific expression of a toxin gene. Cell 50:435–443.

Poethig, R. S. (1987) Clonal analysis of cell lineage patterns in maize embryogenesis. Dev. Biol. 117:392–404

Sanger, T., A. Nicklen and A. R. Coulson (1977) DNA sequencing with chain-termination inhibitors. Proc. Natl. Acad. Sci. U.S.A. 74:5463–5467.

Schwartz, D. and J. Osterman (1976) A pollen selection system for alcohol dehydrogenase-negative mutants in plants, Genetics 83:63–65.

Shimamoto, K. et al. (1989) Nature 338:274–276.

Smith, A. G., C. S. Gasser, K. A. Budelier and R. T. Fraley (1990) Identification and characterization of stamen- and tapetal-specific genes from tomato. Mol. Gen. Genetics. 222:9–16.

Smith, A. G., M.A. Hinchee, and R. Horsch (1987) Cell and tissue specific expression localized by in situ RNA hybridization in floral tissues. Plant Mol. Biol. Reporter. 5:237–241.

Twell, D., J. Yamaguchi and S. McCormick (1989) Pollen-specific gene expression in transgenic plants: coordinate regulation of two different tomato gene promoters during microsporgenesis. Development 109:705–713.

Valvekens, D., M. Van Lijsebettens and M. Van Montagu (1988) Proc. Natl. Acad. Sci. USA 85:5536–5540.

van Tunen, A. J., S. A. Hartman, L. A. Mur and J. N. M. Mol. (1989) Regulation of chalcone flavanone isomerase (CHI) gene expression in *Petunia hybrida*: the use of alternative promoters in corolla, anthers and pollen. Plant Mol. Biol. 12:539–551.

van Tunen, A. J., R. E. Koes, C. E. Spelt, A. R. van der Krol, A. R. Stuitje and J. N. M. Mol (1988) Cloning of the two chalcone flavanone isomerase genes from *Petunia hybrida*: coordinate, light-regulated and differential expression of flavonoid genes. EMBO 7:1257–1263.

Vasil, V., F. Redway and I. Vasil (1990) Bio/Technology 8:429–434.

Yanofsky, M. F., H. Ma, J. L. Bowman, G. N. Draws, K. A. Feldman and E. M. Meyerowitz (1990) Nature 346:35–39.

---

We claim:

1. A recombinant, double-stranded DNA molecule comprising in sequence and operably linked:
   (a) a promoter which functions in plant cells to cause the production of an RNA sequence;
   (b) a structural DNA sequence that causes the production of the phosphonate monoester hydrolase enzyme encoded by the sequence shown in Sequence ID No: 1; and
   (c) a 3' non-translated region which functions in plant cells to cause the addition of polyadenylate nucleotides to the 3' end of the RNA sequence,
said promoter being heterologous with respect to the structural coding sequence.

2. A DNA molecule of claim 1 in which the structural DNA sequence encoding the phosphonate monoester hydrolase has the sequence shown in Sequence ID No: 1.

3. A DNA molecule of claim 2 in which the promoter is the tomato anther 127a promoter.

4. A DNA molecule of claim 3 in which the 3' non-translated region is from the pea ssRUBISCO E9 gene.

5. A DNA molecule of claim 3 in which the 3' non-translated region is from a nopaline synthase gene.

6. A method of producing genetically transformed plants which express a conditional lethal gene, comprising the steps of:

a) inserting into the genome of a plant cell a recombinant, double-stranded DNA molecule comprising in sequence and operably linked
      (i) a promoter which functions in plant cells to cause the production of an RNA sequence;
      (ii) a structural DNA sequence that causes the production of the phosphonate monoester hydrolase enzyme encoded by the sequence shown in Sequence ID No: 1; and
      (iii) a 3' non-translated DNA sequence which functions in plant cells to stabilize and increase expression of the RNA sequence,
said promoter being heterologous with respect to the structural coding sequence;
   (b) obtaining transformed plant cells; and
   (c) regenerating from the transformed plant cells genetically transformed plants which express the phosphonate monoester hydrolase.

7. A method of claim 6 in which the structural DNA sequence comprises a structural coding sequence having the sequence shown in Sequence ID No: 1.

8. A method of claim 7 in which the promoter comprises the tomato anther 127a promoter.

9. A method of claim 8 in which the 3' nontranslated DNA sequence comprises a 3' nontranslated region from the pea ssRUBISCO E9 gene.

10. A method of claim 8 in which the 3' nontranslated DNA sequence comprises a 3' nontranslated region from a nopaline synthase gene.

11. A genetically transformed plant cell comprising a recombinant double-stranded DNA molecule comprising in sequence and operably linked:
   (a) a promoter which functions in plant cells to cause the production of an RNA sequence;
   (b) a structural DNA sequence that causes the production of the phosphonate monoester hydrolase enzyme encoded by the sequence shown in Sequence ID No: 1; and
   (c) a 3' non-translated DNA sequence which functions in plant cells to stabilize and increase expression of the RNA sequence.

12. A cell of claim 11 in which the structural DNA sequence comprises a structural coding sequence having the sequence shown in Sequence ID No: 1.

13. A cell of claim 12 in which the promoter comprises the tomato anther 127a promoter.

14. A cell of claim 13 in which the 3' nontranslated DNA sequence comprises a 3' nontranslated region from the pea ssRUBISCO E9 gene.

15. A cell of claim 13 in which the 3' nontranslated DNA sequence comprises a 3' nontranslated region from a nopaline synthase gene.

16. Genetically transformed plants comprising plant cells containing a recombinant double-stranded DNA molecule comprising in sequence and operably linked:
   a) a promoter which functions in plant cells to cause the production of an RNA sequence;
   (b) a structural DNA sequence that causes the production of the phosphonate monoester hydrolase enzyme encoded by the sequence shown in Sequence ID No: 1; and
   (c) a 3' non-translated DNA sequence which functions in plant cells to stabilize and increase expression of the RNA sequence,
said promoter being heterologous with respect to the structural coding sequence.

17. A plant of claim 16 in which the structural DNA sequence comprises a structural coding sequence having the sequence shown in Sequence ID No: 1.

18. A plant of claim 17 in which the promoter comprises the tomato anther 127a promoter.

19. A plant of claim 18 in which the 3' nontranslated DNA sequence comprises a 3' nontranslated region from the pea ssRUBISCO E9 gene.

20. A plant of claim 18 in which the 3' nontranslated DNA sequence comprises a 3' nontranslated region from a nopaline synthase gene.

* * * * *